United States Patent
Bluecher et al.

(10) Patent No.: US 12,279,944 B2
(45) Date of Patent: Apr. 22, 2025

(54) IMPLANTABLE SUPERHYDROPHOBIC SURFACES

(71) Applicant: BVW Holding AG, Cham (CH)

(72) Inventors: Lukas Bluecher, Eurasburg (DE); Michael Milbocker, Holliston, MA (US)

(73) Assignee: BVW Holding AG, Cham (CH)

( * ) Notice: Subject to any disclaimer, the term of this patent is extended or adjusted under 35 U.S.C. 154(b) by 0 days.

(21) Appl. No.: 17/389,040

(22) Filed: Jul. 29, 2021

(65) Prior Publication Data

US 2021/0353400 A1   Nov. 18, 2021

Related U.S. Application Data

(63) Continuation of application No. 16/368,531, filed on Mar. 28, 2019, now Pat. No. 11,141,260, which is a
(Continued)

(51) Int. Cl.
*A61F 2/92* (2013.01)
*A61F 2/00* (2006.01)
(Continued)

(52) U.S. Cl.
CPC .............. *A61F 2/02* (2013.01); *A61F 2/0063* (2013.01); *A61F 2/0077* (2013.01); *A61L 27/34* (2013.01);
(Continued)

(58) Field of Classification Search
CPC ........ A61F 2/02; A61F 2/0063; A61F 2/0077; A61F 2002/0086; A61F 2002/009;
(Continued)

(56) References Cited

U.S. PATENT DOCUMENTS

| | | | |
|---|---|---|---|
| 5,785,978 A | | 7/1998 | Porter et al. |
| 6,355,198 B1 * | | 3/2002 | Kim ................ B81C 1/00031 |
| | | | 264/299 |

(Continued)

FOREIGN PATENT DOCUMENTS

| | | |
|---|---|---|
| EP | 0628320 A1 | 12/1994 |
| WO | 199618498 A1 | 6/1996 |

(Continued)

OTHER PUBLICATIONS

Zhang, Fengxiang, Jennifer Chan, and Hong Yee Low. "Biomimetic, hierarchical structures on polymer surfaces by sequential imprinting." Applied surface science 254.10 (2008): 2975-2979. (Year: 2008).*

(Continued)

*Primary Examiner* — Emmanuel S Luk
(74) *Attorney, Agent, or Firm* — Patterson Intellectual Property Law, P.C.; Ryan D. Levy; Mark A. Kilgore

(57) ABSTRACT

Bio-adhesive textured surfaces and methods of making the same are described which allow implants to be localized within a living body. Hierarchical levels of texture on an implantable medical device, some capable of establishing a Wenzel state and others a Cassie state, may be employed to interface with living structures to provide resistance to device migration. Since a gaseous state is traditionally required to establish a Cassie or Wenzel state, and gases do not remain long in living tissue, described herein are tissue/device interactions analogous to the above states with the component normally represented by a gas replaced by a bodily constituent, wherein separation of tissue constituents develops and an analogous Cassie, Wenzel, or Cassie-Wenzel state evolves. Further methods of making molds to produce said devices are described herein.

12 Claims, 7 Drawing Sheets

Related U.S. Application Data continuation of application No. 13/745,381, filed on Jan. 18, 2013, now Pat. No. 10,292,806.

(60) Provisional application No. 61/589,907, filed on Jan. 11, 2013.

(51) Int. Cl.
| | | |
|---|---|---|
| *A61F 2/02* | (2006.01) | |
| *A61L 27/34* | (2006.01) | |
| *A61L 27/50* | (2006.01) | |
| *A61L 27/56* | (2006.01) | |
| *A61L 31/10* | (2006.01) | |
| *A61L 31/14* | (2006.01) | |
| *B29C 33/38* | (2006.01) | |

(52) U.S. Cl.
CPC ............... *A61L 27/50* (2013.01); *A61L 27/56* (2013.01); *A61L 31/10* (2013.01); *A61L 31/14* (2013.01); *A61L 31/146* (2013.01); *B29C 33/3842* (2013.01); *A61F 2002/0086* (2013.01); *A61F 2002/009* (2013.01); *A61F 2210/0004* (2013.01); *A61L 2400/18* (2013.01)

(58) Field of Classification Search
CPC .. A61F 2210/0004; A61L 27/34; A61L 27/50; A61L 27/56; A61L 31/10; A61L 31/14; A61L 31/146; A61L 2400/18; B29C 33/3842; G03F 7/0002
See application file for complete search history.

(56) References Cited

U.S. PATENT DOCUMENTS

| | | | |
|---|---|---|---|
| 6,994,045 | B2 | 2/2006 | Paszkowski |
| 7,419,615 | B2 | 9/2008 | Strauss |
| 7,579,077 | B2 | 8/2009 | Dubrow et al. |
| 7,887,736 | B2 | 2/2011 | Lee et al. |
| 9,120,670 | B2 | 9/2015 | Hulseman et al. |
| 9,908,274 | B2 | 3/2018 | Hulseman et al. |
| 9,988,201 | B2 | 6/2018 | Hulseman et al. |
| 10,377,044 | B2 | 8/2019 | Hulseman et al. |
| 10,458,053 | B2 | 10/2019 | Hulseman et al. |
| 10,575,667 | B2 | 3/2020 | Hulseman et al. |
| 10,687,642 | B2 | 6/2020 | Hulseman et al. |
| 10,889,005 | B2 | 1/2021 | Hulseman et al. |
| 2003/0147932 | A1 | 8/2003 | Nun et al. |
| 2004/0224008 | A1 | 11/2004 | Zhang |
| 2005/0053642 | A1 | 3/2005 | Ulbricht et al. |
| 2005/0221072 | A1 | 10/2005 | Dubrow et al. |
| 2006/0029808 | A1 | 2/2006 | Zhai et al. |
| 2006/0240218 | A1 | 10/2006 | Parce |
| 2007/0003705 | A1 | 1/2007 | Strauss |
| 2007/0166513 | A1 | 7/2007 | Sheng et al. |
| 2007/0225785 | A1 | 9/2007 | Park et al. |
| 2008/0015298 | A1 | 1/2008 | Xiong et al. |
| 2008/0057444 | A1* | 3/2008 | Ra ................ B29C 35/0894 430/322 |
| 2008/0226694 | A1 | 9/2008 | Gelbart et al. |
| 2008/0241512 | A1 | 10/2008 | Boris et al. |
| 2009/0001634 | A1* | 1/2009 | Hiroshima ............ G03F 7/2014 264/447 |
| 2009/0011222 | A1 | 1/2009 | Xiu et al. |
| 2009/0076430 | A1 | 3/2009 | Simpson et al. |
| 2009/0227164 | A1 | 9/2009 | Broch-Nielsen et al. |
| 2009/0304992 | A1* | 12/2009 | Desimone ............ G03F 7/0046 428/141 |
| 2009/0324308 | A1 | 12/2009 | Law et al. |
| 2009/0326639 | A1 | 12/2009 | Edin |
| 2010/0021692 | A1 | 1/2010 | Bormashenko et al. |
| 2010/0028604 | A1 | 2/2010 | Bhushan et al. |
| 2010/0086604 | A1 | 4/2010 | Stellacci et al. |
| 2010/0104984 | A1* | 4/2010 | Shiobara ................ B82Y 10/00 430/319 |
| 2010/0112286 | A1 | 5/2010 | Bahadur et al. |
| 2010/0143741 | A1 | 6/2010 | Bell et al. |
| 2010/0168854 | A1 | 7/2010 | Luers et al. |
| 2010/0226943 | A1* | 9/2010 | Brennan ................ B08B 17/06 428/141 |
| 2010/0234945 | A1 | 9/2010 | O'Leary |
| 2010/0276829 | A1* | 11/2010 | Yang .................... B29C 39/003 264/114 |
| 2011/0077172 | A1 | 3/2011 | Aizenberg et al. |
| 2011/0223212 | A1 | 9/2011 | Taton et al. |
| 2011/0270221 | A1* | 11/2011 | Ross .................... B29C 59/026 604/173 |
| 2012/0217220 | A1* | 8/2012 | Dobisz ................. G03F 7/0002 216/41 |
| 2013/0059113 | A1 | 3/2013 | Hatton et al. |
| 2013/0101796 | A1* | 4/2013 | Arzt ........................ B05D 3/12 428/156 |
| 2015/0368838 | A1 | 12/2015 | Hulseman et al. |
| 2017/0014111 | A1 | 1/2017 | Hulseman et al. |
| 2019/0062155 | A1 | 2/2019 | Hulseman et al. |
| 2020/0338808 | A1 | 10/2020 | Hulseman et al. |
| 2021/0086371 | A1 | 3/2021 | Hulseman et al. |

FOREIGN PATENT DOCUMENTS

| | | |
|---|---|---|
| WO | 2011111083 A2 | 9/2011 |
| WO | 2012097891 A1 | 7/2012 |

OTHER PUBLICATIONS

Bhushan, Bharat, and Eun Kyu Her. "Fabrication of superhydrophobic surfaces with high and low adhesion inspired from rose petal." Langmuir 26.11 (2010): 8207-8217. (Year: 2010).*

Park, Yong Min, et al. "Artificial petal surface based on hierarchical micro-and nanostructures." Thin Solid Films 520.1 (2011): 362-367. (Year: 2011).*

Chatzinikolaidou et al. Peri-implant reactivity and osteoinductive potential of immobilized rhBMP-2 on titanium carriers: Acta Biomaterialia 6 (2010) 4405-4421.

Gross, M. et al., "Fall and rise of small droplets on rough hydrophobic substrates." EPL 88 (2009) 26002.

Ishino, C. et al., "Nucleation scenarios for wetting transition on textured surfaces: The effect of contact angle hysteresis," Europhys. Lett., 76(3) pp. 464-470 (2006).

Jennissen, H.P., et al. "Lotus-Effect and inverse Lotus-Effect in connection with extremely rough titanium surfaces." Materialwissenschaft und Werkstofftechnik 41.12(2010):1062-1069.

* cited by examiner

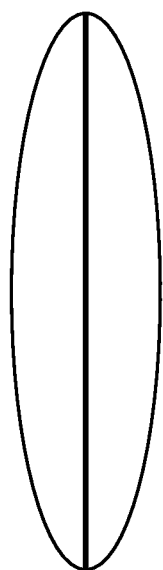 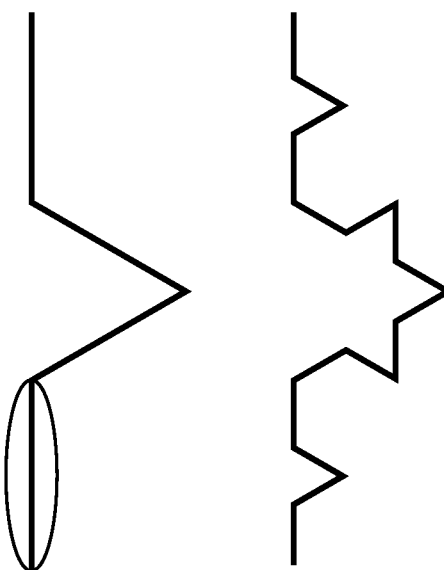 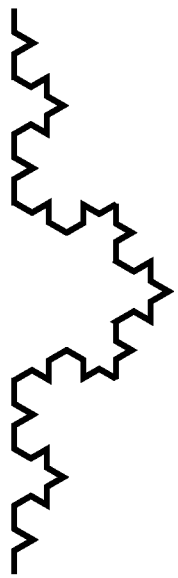
*FIG. 7A*   *FIG. 7B*   *FIG. 7C*   *FIG. 7D*

IMPLANTABLE SUPERHYDROPHOBIC SURFACES

CROSS-REFERENCE TO RELATED APPLICATIONS

This application is a continuation of U.S. patent application Ser. No. 16/368,531 filed Mar. 28, 2019, which is a continuation of U.S. patent application Ser. No. 13/745,381, now U.S. Pat. No. 10,292,806, filed Jan. 18, 2013, which claims the benefit of priority to U.S. Provisional Application No. 61/589,907, filed on Jan. 11, 2013, the contents of which are hereby incorporated by reference in their entirety.

TECHNICAL FIELD

The present disclosure provides implantable medical devices comprising surface textures on a substrate that, upon implantation in a host tissue, create interfaces with liquids present in the host tissue. The implants in certain embodiments advantageously prevent or reduce device migration after implantation into the body.

BACKGROUND

The Cassie and Wenzel phenomena occur classically when three phases are in contact with one another. For example, one can have one solid and two liquid phases in contact, with the two liquid phases being different in their hydrophobicity. In the body, the respective states lead to the formation and retention on an implant of a liquid hydrophilic film in the Cassie state and retention of tissue (containing lipids) in the Wenzel state. These are clinically useful attributes for localizing an implant within living tissue.

Shear is motion of an implant parallel to a tissue surface, and peel is motion of an implant perpendicular to a tissue surface. Clinically, an implant with high shear force resists migration in the body and an implant with low peel force can be repositioned easily by the clinician during the surgical procedure.

The interaction of a solid textured surface with water in a gaseous environment is described by the Cassie-Baxter model. In this model, air is trapped in the microgrooves of a textured surface and water droplets rest on a compound surface comprising air and the tops of micro-protrusions. The importance of a fractal dimension between multiple scales of texture is well recognized and many approaches have been based on the fractal contribution, i.e., the dimensional relationship between different scales of texture. However, regardless of the material (organic or inorganic) used and geometric structure of the surface texture (particles, rod arrays, or pores), multiple scales of texture in combination with low surface energy has been required to obtain the so called super hydrophobic surfaces.

Super hydrophobicity is variously reported as a material exhibiting a contact angle with water that is greater than the contact angles achievable with smooth but strongly hydrophobic materials. The consensus for the minimum contact angle for a super hydrophobic substance is 150 degrees.

A hydrophobic surface repels water. The hydrophobicity of a surface can be measured, for example, by determining the contact angle of a drop of water on a surface. The contact angle can be measured in a static state or in a dynamic state. A dynamic contact angle measurement can include determining an advancing contact angle or a receding contact angle with respect to an adherent species such as a water drop. A hydrophobic surface having a large difference between advancing and receding contact angles (i.e., high contact angle hysteresis) presents clinically desirable properties. Water or wet tissue can travel over a surface having low contact angle hysteresis more readily than across a surface having a high contact angle hysteresis, thus the magnitude of the contact angle hysteresis can be equated with the amount of energy needed to move a substance across a surface in shear. In clinical applications, a high contact angle reduces the mobility of the implant in situ.

The classic motivation from nature for surface texture research is the lotus leaf, which is super hydrophobic due to a hierarchical structure of convex cell papillae and randomly oriented hydrophobic wax tubules, which have high contact angles and low contact angle hysteresis with water and show strong self-cleaning properties. A lesser-known motivation from nature is the red rose petal, with a hierarchical structure of convex cell papillae ornamented with circumferentially arranged and axially directed ridges, which have a moderate contact angle and high contact angle hysteresis.

The contact angle is a measure of the amount of water directly in contact with the implant surface, while the contact angle hysteresis is an inverse measure of the degree to which water is mobile on a surface. The natural evolutionary motivation for each of these states is quite distinct.

In the case of the lotus leaf, and botanical leaves generally, minimal contact with water and high water mobility results in preferential adherence of the water to particulate contaminants, which are cleared from the leave as the water runs off. This serves to reduce light absorbance by surface contaminants and increase photosynthetic efficiency.

In the case of the rose petal, and botanical petals generally as opposed to leaves, most pollinators are attracted to high tension water sources which provide ready accessibility without drowning the insect.

Thus, high contact angle paired with high contact angle hysteresis is preferred where the evolutionary stimulus is reproduction in botanicals, and high contact angle paired with low contact angle hysteresis is preferred where the evolutionary stimulus is metabolism and growth.

Considering for a moment a single texture scale, when water is placed on a textured surface it can either sit on the peaks of the texture or wick into the valleys. The former is called the Cassie state, and the later the Wenzel state. When the Wenzel state is dominant, both the contact angle and contact angle hysteresis increase as the surface roughness increases. When a roughness factor exceeds a critical level, however, the contact angle continues to increase while the hysteresis starts decreasing. At this point, the dominant wetting behavior changes, due to an increase in the amount of air trapped at the interface between the surface and water droplet. In the present context, the gaseous state is replaced with a hydrophobic state; for example, a lipid. The hydrophobic state may be a liquid or a solid derived from the host tissue.

In mixed Wenzel-Cassie states it is possible to have high contact angle and high contact angle hysteresis. However, texture alone is only one aspect, the hydrophobicity of a textured solid relative to the interacting environment is also important.

Water possesses a dipole structure which makes it attractive to any other substance that is charged. Implantable molecules with a charge surplus localized at a specific location on the molecule renders that molecule hydrophilic. In the case of polymers, the charges can associate, and the bulk substance can possess a macroscopic surface charge. And in such macroscopic assemblages, these materials are strongly water attractive. And when those macroscopic charge localities are associated with surface texture, then the implant material becomes super hydrophilic.

Thus, while it is generally advantageous for an implant to be hydrophilic, and associate readily with water in living tissue, this association creates a fluid surface between the implant and the tissue, which acts as a lubricant. Generally, it is disadvantageous for an implant to move from a position determined by a clinician, and generally it is disadvantageous for an implant to require suture or other physical means of localization. Therefore, utilization of an in situ analog to the Cassie-Wenzel state to localize an implant in living tissue is clinically desirable.

BRIEF SUMMARY

It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

The present disclosure provides an implantable medical device comprising at least two surface textures on a substrate, wherein upon implantation in a host tissue, the surface textures form interfaces with liquids present in the host tissue, wherein a part of the surface texture contacts lipids present in the host tissue to form a first interface; a part of the surface texture contacts water present in the host tissue to form a second interface; and a part of the surface texture traps air between the device and the host tissue; wherein the resulting interfaces have a contact hysteresis angle of at least 5 degrees.

The methods and embodiments of the disclosure are applicable to absorbable and permanent implantable materials, where absorbable materials are preferred. The disclosure relates to physiologically absorbable, non-fibrogenic, hydrophilic materials that are made relatively hydrophobic during a first time interval by the addition of surface texture. Alternatively, the disclosure relates to physiologically absorbable, generally fibrogenic, hydrophobic materials that are made relatively hydrophilic during a first interval by the addition of surface texture. These surface textures are employed to localize these implants within a living body.

The disclosure relates to implantable, absorbable sheets which are hydrophilic, and possibly swell or even dissolve in situ, whereby the addition of a surface texture increases the force threshold for dislocation of a device after implantation.

Furthermore, the disclosure relates to implantable sheets with one side with an enhancement as described with respect to a first particular purpose and a second side with an enhancement as described with respect to a second particular purpose.

The disclosure relates to implantable devices with surface textures possessing an affinity for tissue, which allows them to be pealed from a tissue surface and repositioned perioperatively but resists sliding and folding after implantation.

One object of the present disclosure is to provide implantable medical devices comprising surface textures that initially create classical Cassie and Wenzel states when exposed to an aqueous environment in a mammalian body. Furthermore, implantable medical devices disclosed herein may form analogs to Wenzel and Cassie states after a period of time in the host tissue that involve a solid hydrophilic phase, a liquid hydrophobic phase, and a liquid hydrophilic phase. In these modified Wenzel and Cassie states, the trapped phase analogous to the classical gaseous phase is the host derived hydrophobic phase.

Further provided herein are implantable medical devices comprising textures that after a period of time after implantation replace a gaseous phase with a solid hydrophobic phase. Implantable, absorbable sheets comprised of a hydrophilic substrate that can swell or even dissolve in situ, whereby the addition of a hydrophobic surface texture reduces the rate of absorption or conformal change in situ.

For example, implantable, absorbable sheets comprising a hydrophilic substrate are provided, that can possibly swell or even dissolve in situ, whereby the addition of a hydrophobic surface increases the force required to translate, rotate, fold, or shrink the area of an implant.

Further provided herein are implantable medical devices, wherein the dominance of the Wenzel state over the Cassie state, or the converse, or their analogues, can evolve as a function of time as the outer surfaces of the device are removed by hydrolysis or enzymatic degradation.

Further provided herein are implantable medical devices, wherein accentuation of surface charge and surface energy occurs whereby such that water is always in association with the implant surface, even though any particular water molecule may have a short residence time on the implant surface.

In further embodiments, implantable medical devices are provided, wherein tissue interaction of the implant surface results in tissue association with the implant surface, and in particular implant association with a lipid constituent of the tissue.

In particular, the disclosure describes a surface super hydrophobic effect wherein resistance to implant sliding, rolling, folding or other conformal changes of an implantable medical device is resisted.

BRIEF DESCRIPTION OF THE DRAWINGS

FIG. 7A-7D. Examples of Kock snowflake surface texture.

DETAILED DESCRIPTION

Figure 1A:
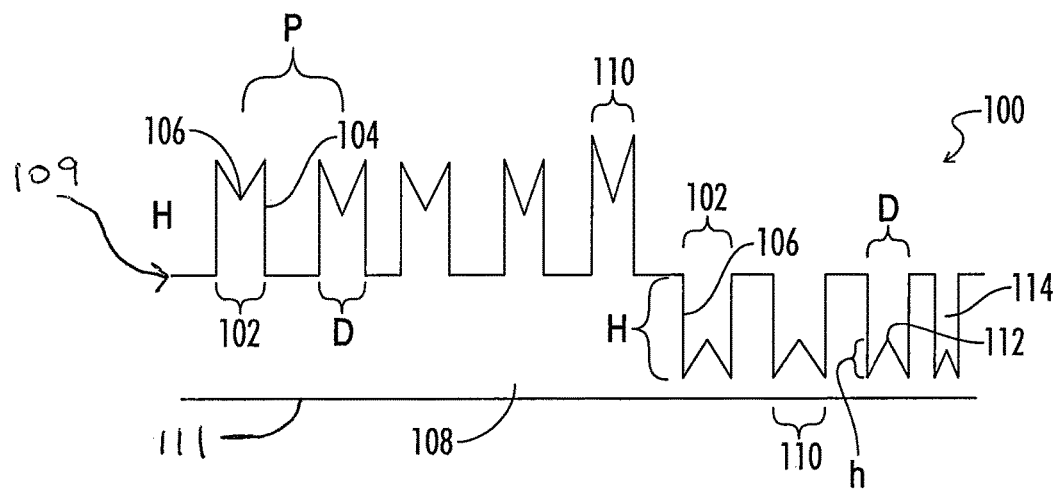
FIG. 1A-B. General view of an implantable prosthetic of the present disclosure possessing a hierarchical surface.

Reference now will be made in detail to the embodiments of the present disclosure, one or more examples of which are set forth herein below. Each example is provided by way of explanation of the embodiments of the present disclosure and is not a limitation. In fact, it will be apparent to those skilled in the art that various modifications and variations can be made to the teachings of the present disclosure without departing from the scope or spirit of the disclosure. For instance, features illustrated or described as part of one embodiment, can be used with another embodiment to yield a still further embodiment.

Thus, it is intended that the present disclosure covers such modifications and variations as come within the scope of the appended claims and their equivalents. Other objects, features and aspects of the present disclosure are disclosed in or are obvious from the following detailed description. It is to be understood by one of ordinary skill in the art that the present discussion is a description of exemplary embodiments only and is not intended as limiting the broader aspects of the present disclosure.

One embodiment provides an implantable medical device comprising at least two surface textures on a substrate, wherein upon implantation in a host tissue, the surface textures form interfaces with liquids present in the host tissue, wherein a part of the surface texture contacts lipids present in the host tissue to form a first interface; a part of the surface texture contacts water present in the host tissue to form a second interface; and a part of the surface texture traps air between the device and the host tissue; wherein the interfaces have a contact hysteresis angle of at least 5 degrees.

The medical devices may comprise the surface texture material, or the medical devices may comprise other materials commonly used in the art having the surface texture material disposed thereon. The surface texture refers to a microscale texture or pattern disposed in the substrate material, for example, as described by the methods described herein below. In particular embodiments, the surface texture comprises a hierarchical structure.

In particular embodiments, the contact hysteresis angle ranges from at least 5 degrees to about 90 degrees. In other embodiments, the contact hysteresis angle ranges from at least 5 degrees to about 75 degrees, while in further embodiments, the contact angle hysteresis ranges from about 10 degrees to about 75 degrees.

In another embodiment, after a period of time after implantation, trapped air is replaced by lipids derived from the host tissue. Furthermore, in some embodiments, after a period of time, the interfaces comprise: a) a solid hydrophilic phase, b) a liquid hydrophobic phase, and c) a liquid hydrophilic phase. In yet another embodiment, the implantable medical device of claim 1, wherein the trapped air is replaced by a liquid hydrophobic phase after a period of time. In other embodiments, after a period of time, the trapped air is replaced by a hydrophobic material derived from host tissue. For example, the period of time may be about 5 minutes to 12 hours, or more particularly, about 5 minutes to about 6 hours, or about 30 minutes to about 6 hours.

The implantable medical devices provided herein advantageously resist migration in the body after implantation. For example, in some embodiments, the shear force to translate the device relative to host tissue exceeds about 50 grams per square centimeter. In certain embodiments, the shear force may range from about 50 to about 200 grams per square centimeter, about 50 to about 150 grams per square centimeter, or about 70 to about 150 grams per square centimeter.

In another embodiment, the surface textures comprise hydrophilic absorbable materials, wherein the hydrophilic absorbable materials are made less hydrophilic by the surface textures, and the surface textures reduce the rate of absorption or conformal change of the medical device in the host tissue. In other embodiments, the surface textures comprise hydrophobic absorbable materials, wherein the hydrophobic absorbable materials are made less hydrophobic by the surface textures, and the surface textures increase a rate of absorption or conformal change of the medical device in the host tissue.

In other embodiments, at least one surface texture comprises absorbable materials, wherein the at least one surface texture is modified by absorption, such that the at least one surface texture becomes more wetting or less wetting as the medical device is absorbed.

In certain embodiments, wherein the surface textures have a rate of absorbance in the host tissue that mitigates tissue adhesion and implant migration in a first time interval and becomes smooth, hydrophilic, rapidly absorbing and non-fibrogenic material in a second time interval. For example, a first time interval may range from about 5 minutes to about 6 hours, or about 10 minutes to about 6 hours, about 10 minutes to about 3 hours, or about 10 minutes to about 30 minutes, and a second time interval may range from about 30 minutes to about 12 hours, about 30 minutes to about 6 hours, about 1 hour to about 6 hours or about 3 hour to about 6 hours.

In certain embodiments, at least one surface texture comprises a smaller pitch of 10 nanometers to 1 micron, and another surface texture comprises a pitch of 2 microns to 100 microns, wherein the smaller surface texture is disposed on the larger surface texture, such that a hierarchical structure is provided. In some embodiments, the smaller surface textures trap the air, while the larger surface texture does not trap air. In a different embodiment, the larger surface texture traps air and the smaller surface texture does not trap air. The interfaces thus formed depend in part on the pitch size, the pattern of the texture, and/or the substrate material used to prepare the surface texture, as described in more detail hereinbelow. In a particular embodiment, the first interface excludes attachment of a first host derived substance and the second interface promotes attachment of a second host derived substance. For example, the first host derived substance may be a microbe and the second host derived substance may be host cells. In another example, the first host derived substance is a protein and the second tissue derived substance is host tissue. In certain embodiments, the first host derived substance is hydrophobic for one texture and the second host derived substance is hydrophobic for a different texture. In other embodiments, the first host derived substance is a protein and the second host derived substance is host tissue.

In further embodiments, upon implantation in the host tissue, a surface charge of at least one surface texture increases such that water is more strongly bonded to the substrate surface, but not so strongly bonded so as to preclude exchange of water molecules bonded to said substrate surface with surrounding water in the host tissue. For example, a layer of water may adhere to the surface of the device and said water layer reduces the rate of protein molecule adsorption to said textured surface, relative to a device comprised of said substrate without surface texture. Furthermore, a layer of water may adhere to the surface textures of the device, such that the water layer reduces a rate of protein molecule adsorption to the textured surface, relative to a device without the surface textures.

In particular embodiments, the substrate may be porous. For example, the substrate may comprise three-dimensionally interconnected pores.

In some embodiments, the first surface texture forms a Cassie state when implanted in host tissue and the second surface texture forms a Wenzel state when implanted in host tissue. In further embodiments, at least one of the surface textures comprises fibers embedded in and protruding from the substrate, and the fibers are bifurcated at least once on at least one spatial scale different from a pitch of other surface textures of the device. In yet another embodiment, at least one of said surface textures is comprised of fibers embedded at both ends in said substrate and said fiber and protrude from said substrate and said fibers form loops with at least one diameter different from the pitch of other surface textures of the medical device.

In certain embodiments, the surface textures may comprise or be similar to certain mathematical fractal shapes. For example, in some embodiments, at least one surface texture comprises a Koch snowflake pattern, a Sierpinski gasket pattern, Apollonian gasket pattern, or a diffusion limited aggregation pattern.

In certain embodiments, the aforementioned implantable medical devices comprise two sides, such as a sheet structure, wherein the two sides have different surface texture patterns. In one embodiment, the surface textures form interfaces with liquids present in host tissue, wherein at least one surface texture traps air between the device and tissue and at least one other surface texture does not trap air between the device and tissue, and wherein the resulting interfaces generate a contact hysteresis angle of at least 5 degrees on one side (for example, the contact angle hysteresis can be at least 5 degrees to about 90 degrees, at least 5 degrees to about 75 degrees, or about 10 degrees to about 75 degrees), and less than 5 degrees (for example, an angle of about 0.1 to less than 5 degrees, or more particular, about 0.5 to less than 5 degrees, or more particularly, about 0.5 to about 3 degrees) on the other side of the device.

It should be understood that the structures of the present disclosure are not intended to be strictly superhydrophobic and should not be limited on that basis. For example, a typically hydrophilic material can be rendered more hydrophobic by the addition of surface structure, but such addition does not require the surface to be superhydrophobic, by the usual definitions.

While not being bound by any particular theory, the implantable medical devices can be further understood as explained by the principles described below. A scale of interaction is defined by the spatial dimensions of a surface texture of an implantable device. In certain embodiments, the surface texture hierarchical, meaning one texture of a given dimension is applied upon a second texture of larger dimension. A hierarchical design is characterized by at least two spatial scales. One scale is typically on the order of 10's of micrometers (microns) and another on the order 100's of nanometers up to a few microns. The surface texture may induce one state with a large difference between preceding and receding contact angles (contact angle hysteresis), or alternatively another state with a small contact angle hysteresis. States of interest, and there in situ analogues, are known respectively as Wenzel and Cassie states. Each of the hierarchical spatial scales may induce separately a Wenzel or Cassie state, such that combinations are possible on a multiplicity of spatial scales.

These states are typically characterized by three phase contacts, and classically consist of solid, liquid, and gaseous phases. These phase contacts are initiated by the dimensionality of the surface texture. Since the gaseous component eventually dissipates in vivo by a combination of liquid evaporation into the gaseous domain and gas dissolution into the liquid domain, the Cassie state could eventually evolve into the Wenzel state in living tissue.

The present disclosure relates to implantable materials comprised of textures that initially create Cassie and Wenzel states when exposed to an aqueous environment in a mammalian body. These states evolve in situ, and their evolution analogues differ from typical Wenzel and Cassie states in that they involve a solid hydrophilic phase, a liquid hydrophobic phase, and a liquid hydrophilic phase or a solid hydrophobic phase, a liquid hydrophilic phase, and a liquid hydrophobic phase. In these modified Wenzel and Cassie states, the trapped phase analogous to the classical gaseous phase is the liquid hydrophobic phase. Alternatively, a trapped gaseous phase is preferentially replaced by a liquid hydrophilic phase. In this alternative construction, at least one of the other phases is hydrophobic.

The Cassie and Wenzel phenomena, occur classically when three phases are in contact with one another. For example, one can have one solid and two liquid phases in contact, with the two liquid phases being different in their hydrophobicity. In the body, the respective states lead to the formation and retention on an implant of a liquid hydrophilic film in the Cassie state and retention of tissue (containing lipids) in the Wenzel state. These are clinically useful attributes for localizing an implant within living tissue.

In the Cassie state the implant is resistant to cellular adhesion. In the Wenzel state the implant is reversibly adherent to tissue. In hybrid Cassie-Wenzel states, where one texture scale is Wenzel and the other is Cassie, the implant can be both localizing in shear to a tissue surface and releasable in peal. Shear is motion of an implant parallel to a tissue surface, and peal is motion of an implant perpendicular to a tissue surface. Clinically, an implant with high shear force resists migration in the body and an implant with low peal force can be repositioned easily by the clinician during the surgical procedure.

Opposite sides of an implant may be biased toward tissue localization on one side and resistant to tissue adhesion on the other side, while both sides may exhibit both properties to greater or lesser extent. The dominance of Wenzel over Cassie, or the converse, can evolve as a function of time as the outer surfaces of the implant are removed by hydrolysis or enzymatic degradation. In particular cases, the spatial frequency of the various structure scales may be modulated within the implant, such that as the implant dissolves it presents a changing spatial frequency as the surface layers of the implant are removed.

Alternatively, the surface texture may be chosen such that one side has high surface area relative to a second side with low surface area.

Alternatively, the surface texture may be chosen to modulate the hydrophobicity of a single implant material to control water absorbance, biodegradation, and drug elution differentially relative to regions or whole sides of the implant.

The interaction of a solid textured surface with water in a gaseous environment is described by the Cassie-Baxter model. In this model, air is trapped in the microgrooves of a textured surface and water droplets rest on a compound surface comprising air and the tops of micro-protrusions. The importance of a fractal dimension between multiple scales of texture is well recognized and many approaches have been based on the fractal contribution, i.e., the dimensional relationship between different scales of texture. However, regardless of the material (organic or inorganic) used and geometric structure of the surface texture (particles, rod arrays, or pores), multiple scales of texture in combination with low surface energy has been required to obtain the so called super hydrophobic surfaces.

Super hydrophobicity is variously reported as a material exhibiting a contact angle with water that is greater than the contact angles achievable with smooth but strongly hydrophobic materials. The consensus for the minimum contact angle for a super hydrophobic substance is 150 degrees, so in this context most of the embodiments of the present disclosure are not strictly super hydrophobic because our end state is not a classical gas entrapping state, but rather the gas is replaced by a hydrophobic phase.

A hydrophobic surface repels water. The hydrophobicity of a surface can be measured, for example, by determining the contact angle of a drop of water on a surface. The contact angle can be measured in a static state or in a dynamic state. A dynamic contact angle measurement can include determining an advancing contact angle or a receding contact angle with respect to an adherent species such as a water drop. A hydrophobic surface having a large difference between advancing and receding contact angles (i.e., high contact angle hysteresis) presents clinically desirable properties. Water or wet tissue can travel over a surface having low contact angle hysteresis more readily than across a surface having a high contact angle hysteresis, thus the magnitude of the contact angle hysteresis can be equated with the amount of energy needed to move a substance across a surface in shear. In vivo, a high contact angle reduces the mobility of the implant in situ.

One motivation for surface texture research is the lotus leaf, which is super hydrophobic due to a hierarchical structure of convex cell papillae and randomly oriented hydrophobic wax tubules, which have high contact angles and low contact angle hysteresis with water and show strong self-cleaning properties. An explored structure is the red rose petal, with a hierarchical structure of convex cell papillae ornamented with circumferentially arranged and axially directed ridges, which have a moderate contact angle and high contact angle hysteresis.

Considering for a moment a single texture scale, when water is placed on a textured surface it can either sit on the peaks of the texture or wick into the valleys. The former is called the Cassie state, and the later the Wenzel state. When the Wenzel state is dominant, both the contact angle and contact angle hysteresis increase as the surface roughness increases. When a roughness factor exceeds a critical level, however, the contact angle continues to increase while the hysteresis starts decreasing. At this point, the dominant wetting behavior changes, due to an increase in the amount of air trapped at the interface between the surface and water droplet. In the present context, the gaseous state is replaced with a hydrophobic state; for example, a lipid. The hydrophobic state may be a liquid or a solid derived from the host tissue. In mixed Wenzel-Cassie states it is possible to have high contact angle and high contact angle hysteresis.

Water possesses a dipole structure which makes it attractive to any other substance that is charged. Implantable molecules with a charge surplus localized at a specific location on the molecule renders that molecule hydrophilic. In the case of polymers, the charges can associate, and the bulk substance can possess a macroscopic surface charge. And in such macroscopic assemblages, these materials are strongly water attractive. And when those macroscopic charge localities are associated with surface texture, then the implant material becomes super hydrophilic.

The term super hydrophilic has various meanings in the literature, and in many cases simply refers to the rendering of a substance more hydrophilic, or a decrease in contact angle relative to a flat surface of the same substance. Here, it is meant the accentuation of surface charge and surface energy such that water is always bonded to the substrate surface, even though any particular water molecule may have a short residence time on the implant surface.

It should be understood that none of the structures of the present disclosure are intended to be strictly super hydrophobic in the classical sense when implanted and should not be limited on that basis. For example, a typically hydrophilic material can be rendered more hydrophobic by the addition of surface structure, but such addition does not require the surface to be super hydrophobic, by the usual definitions. In particular, a super hydrophobic surface in contact with liquid in open air is not super hydrophobic when implanted in a wet environment such as living tissue. Thus, while the present disclosures are super hydrophobic outside the body, they are not super hydrophobic when implanted.

A surface is defined as super hydrophobic when the water contact angle is greater than 150 degrees in open air. The highest contact angle for a water droplet on a smooth surface is dictated by the electronic structure of the molecules comprising the smooth surface and is approximately 120 degrees. For example, $CF_3$ groups have a low surface energy of 6.7 mJ/m$^2$.

Beyond a contact angle of 120 degrees, the fine surface roughness becomes the dominant factor in increasing the contact angle. The mechanisms responsible for the effect of surface roughness were addressed by Wenzel and later by Cassie and Baxter. Thus, a super hydrophobic surface must possess a surface roughness. It is possible to render hydrophilic substances hydrophobic by use of texture. The following are original derivations of contact angles and design principles for implant environments, and thus are not generally know, and constitute teaching of the present disclosure.

The interaction of water with a smooth surface is characterized by Young's angle θy, and the wettability is quantified by the Young equation, $$\cos \theta y = (\gamma s\text{-}g - \gamma l\text{-}s)/\gamma l\text{-}g,$$

where γs-g, γl-s, and γl-g represent the interfacial tensions of solid-gas, s-g, liquid-solid l-s, and liquid-gas, l-g interfaces, respectively.

For a textured surface, there are two water contact states corresponding first to water filling the interstitial sites (Wenzel) and second gas trapped in the interstitial sites by a layer of water (Cassie). For textured surfaces with a multiplicity of surface texture spatial scales it is possible for the larger scaled texture to form contact with water in the Wenzel state and for smaller scale texture to form contact with water in the Cassie state. This mixed water contact state is commonly called the Cassie wettable state, or the Cassie-Wenzel state.

A characterization of the Wenzel state can be obtained by generalizing the Young equation as follows:

$$\cos \theta a, w = r \cos \theta y,$$

where r is termed the "roughness factor" and defined as the ratio of the actual area of contact on a rough surface to the projected area of contact in the contact plane A characterization of the Cassie state can be obtained by generalizing the Young equation as follows $$\cos \theta a, c = rf \cos \theta y + f - 1,$$

where f represents the fraction of the projected area that is wetted by the liquid. These equations relate surface energy to the geometry of solid/liquid interface in equilibrium. In the implant environment, nothing is static, and the Brownian motion of different chemical constituents is responsible for repeated association and disassociation with a surface. The surface may itself be changing where a portion or all of a surface is absorbable.

When the energy to form a liquid/solid interface is different from the energy to remove a liquid/solid interface, then their contact angles are different, and this difference is called contact angle hysteresis. Contact angle hysteresis is defined here as the difference between association and disassociation contact angles. This hysteresis occurs due to the wide range of "metastable" states which can be observed as the liquid surface tension interacts with the surface of a solid at the phase interface.

The adhesive aspect of the "petal effect", a Cassie wettable state, is one in which the energy to associate a liquid with a surface is less than the energy required to disassociate that interface, even in cases where the overall surface energy is quite low (high contact angle). The contact angle hysteresis is achieved by allowing one scale of roughness to be Wenzel and another scale of roughness to be Cassie. When all scales of roughness are Cassie (non-wetting), then formation of a liquid/solid interface requires relatively more energy than for the Cassie wettable state, and the association of liquid/solid contact and the disassociation of liquid/solid contact are approximately equally disfavored (low contact angle hysteresis). This results in the "lotus effect" where liquid/solid interface comprises low surface area and is easily disassociated.

Thus, the lotus (Cassie) and petal (Cassie wettable) effects can be characterized by the following equation:

$$\cos \theta a = Q1 \cos \theta 1 \pm Q2 \cos \theta 2$$

which describes the effect of surface heterogeneity on the contact angle. In this equation, $\theta a$, the apparent angle, is the weighted average of the contact angles of two roughness scales on the surface. This equation can be generalized to any number of scale hierarchies. The quantities Q1 and Q2 represent the fraction of the surface covered by liquid/solid interface for each of the roughness scales characterized by contact angles $\theta 1$ and $\theta 2$. When $\theta 1$-$\theta 2$ is large (contact angle hysteresis), $\theta a$ characterizes a petal effect and is generally adhesive. When $\theta 1$-$\theta 2$ is small, $\theta a$ characterizes a lotus effect and is generally repulsive.

Thus, for the petal state one of the $\theta$ is $\theta ac$ (Cassie) and the other $\theta$ is $\theta aw$ (Wenzel) and for the lotus state both of the $\theta$ are $\theta ac$ (Cassie). For example, setting $\theta 1 = \theta ac$ and $\theta 2 = \theta aw$, then the complete equation is $$\cos \theta a = Q1 \cos \theta ac \pm Q2 \cos \theta aw = Q1(rf \cos qy + f - 1) \pm Q2(r \cos qy)$$

Note that the contact angle is determined by both a) the hydrophobicity/hydrophilicity (surface electronic structure) of the substance comprising the surface and b) its texture. The above equation assumes the solid surface is comprised of a single substance and represents only the hierarchical structure of the surface texture.

Now consider a solid surface with both hierarchical surface texture and hierarchical changes in surface hydrophobicity. Thus, the apparent angle $\theta ac$ or $\theta aw$ is a function of both structure scale and surface electronic structure. Thus, spatial structure and electronic structure are interchangeable when $$\theta ac(\text{spatial}) = \theta ac(\text{electronic})$$

$$\theta aw(\text{spatial}) = \theta aw(\text{electronic})$$

$\theta a$ (spatial) is dependent solely on the Young equation, accordingly the most general equation for the apparent contact angles is $$\cos \theta a = \Sigma_{i=i,n}[Q_i(rf_i \cos \theta y_i + f_i - 1)] \pm \Sigma_{i=n+1,m} Q_i(r_i \cos \theta y_i).$$

In the implant environment the surface of a solid is modified by relatively amphiphilic aqueous constituents residing in the body. The implant/tissue interfacial tension can be modified by amphiphilic constituent addition caused by the adsorption of amphiphilic proteins onto the implant and can be described by the Gibbs adsorption equation, which relates the surface excess concentration $\Gamma s$ to the interfacial tension $\gamma$ by $$\Gamma s = -(1/k_B T)(d\gamma/d \ln c_p).$$

Where $c_p$ is the surface protein concentration, T is temperature and $k_B$ is the Boltzmann constant.

When $c_p$ exceeds a critical density the protein monolayer of l-g or l-s interface becomes saturated, because both $\gamma$l-g and $\gamma$l-s are unchanged. In vivo constituents are unable to reduce $\gamma$l-s further to satisfy the condition, $\gamma$l-s<$\gamma$s-g, at saturation and thus the surface remains in a hydrophobic range. Since the l-s interface is saturated before the l-g interface is, contact angle reduction for in vivo constituents is controlled by surface tension ($\gamma$l-g). Contact angle hysteresis is generally increased with the surface protein concentration. Nonetheless, like the associated contact angle, contact angle hysteresis evolves to be independent of surface protein concentration as $c_p$ approaches the critical protein density.

The above equations provide the means to design an implant with a surface which stays adhesive in the shear direction after implantation.

The present disclosure is directed to adapting the super hydrophobic effect and related petal and lotus effects and in particular wettable Cassie and pure Cassie states to an implant environment. Therefore, except where polymers are used which actively entrap a gas state on an implant surface (and those will be considered here), a gas state cannot be relied upon to create the desired Cassie states. Biological fluids are far from homogeneous, and are comprised of discrete hydrophilic and hydrophobic components, suspended macromolecules, and several size scales of sub-cellular, cellular, and tissue structures.

The present application describes methods and devices which use Cassie states that organize constituents of a liquid biologic medium to create an adhesive effect. These methods comprise the use of scale hierarchical surface geometry, scale hierarchical regions of surface hydrophobicity/hydrophilicity, and scale hierarchical regions of hydrophobic phase adhesion.

According to this disclosure, it is proposed to use spatially hierarchical surfaces as regards their geometry. In particular, surface textures that are linearly and fractally arranged in a scale ranging from tens of micrometers down to several nanometers. Considering that only the outermost portions of individual hierarchic levels are wetted (contact water), such structures should be characterized by a very small surface of effective contact between the solid and bodily aqueous fluids, preferably below 1% of the implant surface.

It should be understood that at any one scale, the percentage of water association is critical, and not the absolute value of the amount of water association, such that at various fine scales the amount of water interaction with the surface may be very small or very large. The clinical consequence could be great relative to the percentage of water that is interacting with the local surface structure, even if most of the surface is in contact with water. Conversely, in the non-contact area and where air is initially trapped, lipid constituents are preferentially attracted, particularly tissue constituents of lipophilic character, which preferably replace the regions occupied by air.

In at least one embodiment of the present disclosure lipid films originating from the body attach to the implant, the result is that the film acts as a low energy surface which energetically disfavors translation of the implant parallel to the interfacial tissue surface. In particular, such films, some of which may be proteinaceous and hydrophobic, may undergo denaturation or polymerization, which acts as a glue to localize an implant.

In particular, an embodiment of the present disclosure is an implanted surgical barrier, one side of one side of which possesses a Cassie wettable state for localizing the implant to tissue, and the other side possesses a pure Cassie state for resisting tissue adhesions.

In another embodiment, the substrate material may have on one side a layer which is relatively rapidly absorbable and hydrophilic and on the other side is a layer which is relatively slowly absorbed and hydrophobic such that the texture on the two sides produce a Cassie wettable state on one side and a super hydrophobic pure Cassie state on the other side.

In another embodiment, the Cassie wettable state induces denaturation or polymerization of aqueous dissolved proteins.

In another embodiment, the tissue adhesive surfaces of the present disclosure bind to tissue spontaneously in the presence of water. Without wishing to be bound by theory, it has been reported that hydrophobic bonding is based on very-long-range attractive forces. These forces are due to lipid separation resulting in a phase-like transition in bodily fluid present at an implant site. This change is characterized by a sudden, strong attractive force and by the formation of lipid bridges. In contradistinction, implantables with long-range attractive forces are described.

In another embodiment of the present disclosure, such attractive forces between a textured implant surface and tissue are employed to (reversibly) bind an implant to a surgical site.

In another embodiment, the surface texture of an implant may be chosen to induce a filtering effect, wherein certain molecules, cellular structures, or tissue components are attracted while others (particularly water) are repelled, and this attractive/repulsive effect varies across different surface texture spatial scales. This screening effect permits a longer duration adhesive aspect by replacing initially trapped air with a lipid fraction. The lipid fraction may be connective tissue rather than a liquid lipid fraction.

The present patent introduces the concept of using structured surfaces consisting of non-communicating (closed cell) roughness elements to prevent the transition of trapped air to a hydrophilic fluidic mobile state characterized by transition from the Cassie to the Wenzel state. The resistance to the Cassie to Wenzel transition can be further increased by utilizing surfaces with nanostructured (instead of microstructured) non-communicating elements, since the resistance is inversely related to the dimension of the roughness element.

One aspect of some embodiments of the present disclosure are dimpled or impressed surfaces that offer increased resistance to droplet transition to the Wenzel state compared to a dimensionally equivalent pillared surface. The presence of air trapped inside the non-communicating craters and the resistance to fluid motion offered by the crater boundaries and corners contribute to this increased resistance to the transition to a Wenzel state and enhance adhesiveness in vivo.

The impressed or concave textured surfaces of the present disclosure preferably possess a fractal structure or hierarchic structure, wherein the first hierarchic level is located next to the coating substrate and each successive level is located on the surface of forms of the previous hierarchic level and the shape of forms of higher hierarchic levels reiterate the shapes of lower hierarchical levels and the structure contains forms of at least two hierarchical levels.

The substrate of the biocompatible implants of the present disclosure are polymeric materials with possibly one or more nano-scale textures (up to 10 microns) with dimensional spacing of 10 to several thousand nanometers and at least one micro-scale texture with dimensional spacing of 10 to about 100 microns.

The polymeric material is preferably heat meltable without decomposition or alternatively soluble in a solvent, so that the texture may be embossed in the melt state or cast in the solvent state.

Generally, texture refers to topographical and porosity elements, including elevations and depressions on the surface and mass distribution in the volume of a polymeric surface and of the layer comprising the surface. The polymeric layers may be made of multiple polymer types, and may contain other material being embedded in the polymer and contributing to the topography, For example, non-polymeric or polymeric fibers or particulate may be dispersed on the surface of the polymer substrate, these fibers may comprise more phases or components. In particular, the fiber or particulate components may possess absorption rates in a mammalian body slower than the bulk polymer such that a desired texture is preserved for an extended period during the dissolution process. Alternatively, these slower absorbing elements are embedded in the polymeric substrate homogeneously or on several levels such that several different topologies are presented during the course of dissolution.

The textured implants of this disclosure can have many variants and combinations that are specified as follows. For example, the implant can have a homogenous bulk composition wherein grooves, ridges, protuberances or indentations are located, on at least two spatial scales, on the surface of implant. The implant can have a porous substrate with three dimensionally interconnected pores. The implant can have a solid substrate with interconnected channels or non-interconnected indentations on the implant surface. The implant can have a first small scale texture embossed on a second larger scale structure, or a hierarchical arrangement of such scales. The implant can have a first small scale texture that is concave and non-communicating embossed on a second larger scale structure that is convex and communicating, or a hierarchical arrangement of such structures. The implant can have a first small scale texture that is Cassie embossed on a second larger scale structure that is Wenzel, or the reverse. The implant can have grooves or ridges deployed in a step-like contour on larger scale convex protuberances. The implant can have a semi-open structure wherein hierarchical texture is located on cross elements, such that the semi-open structure itself comprises a texture. The implant can have fibers imbedded and protruding from the polymer substrate, said fibers can be bifurcated on a number of spatial scales in the manner of the fibers disposed on a Gecko foot. The implant can have fibers attached by both ends in the polymeric substrate, thus determining loops, the radius of said loops of at least two length scales. The implant can have any combination of the above.

In describing the hierarchical structures of the present disclosure, "protuberance" refers to any higher structure on a macroscopically planar surface and "depression" refers to any lower structure on a macroscopically planar surface. Generally, protuberances and depressions are paired with respect to a specific spatial scale, and reported dimensions thereof are made pair-wise. For example, when a protuberance is reported to be 100 microns in height, that dimension is measured with respect to a near-by depression. In engineering parlance, the measurement is made peak to trough. Lateral measurements are typically made peak to peak or trough to trough, and are referred to as the pitch.

For the purposes of promoting an understanding of the principles of the disclosure, reference will now be made to the embodiments illustrated in the drawings and specific language will be used to describe the same. It will nevertheless be understood that no limitation of the scope of the disclosure is thereby intended, such alterations and further modifications in the illustrated device, and such further applications of the principles of the disclosure as illustrated therein being contemplated as would normally occur to one skilled in the art to which the disclosure relates.

At least one embodiment of the present disclosure will be described and shown, and this application may show and/or describe other embodiments of the present disclosure. It is understood that any reference to "the disclosure" is a reference to an embodiment of a family of disclosures, with no single embodiment including an apparatus, process, or composition that must be included in all embodiments, unless otherwise stated.

Figure 1B:
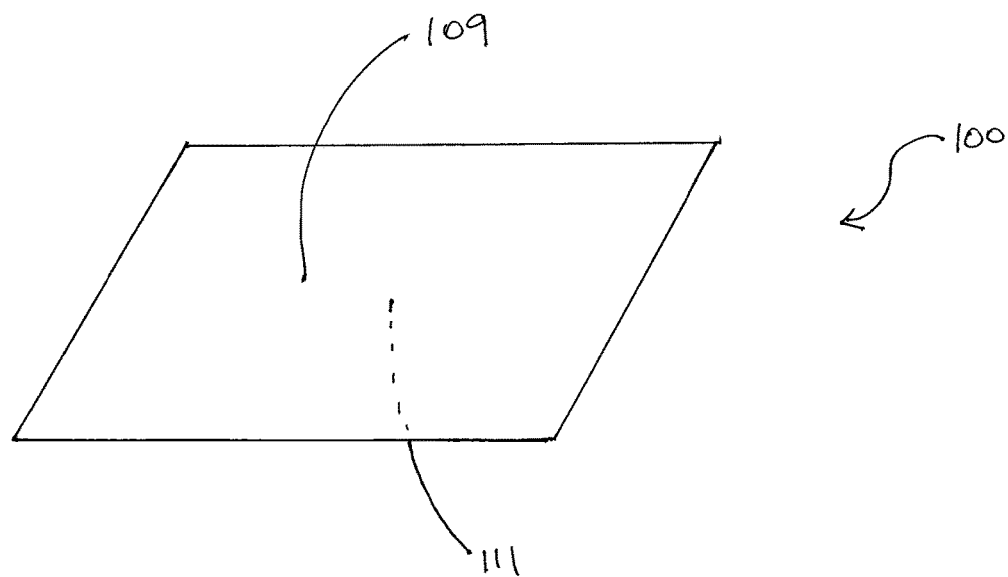

Referring to FIG. 1A, an implantable prosthetic 100 of the present disclosure possesses a hierarchical surface comprised of a micro-scale structure 102 with a plurality of protuberances 104 and depressions 106 disposed in a geometric pattern on at least one surface of a substrate 108, and a nano-scale structure 110 disposed on at least one surface of the micro-level structure 102. The nano-scale structure 110 is similarly comprised of protuberances 112 and depressions 114. The implantable prosthetic 100 may include a first surface 109 and a second surface 111, as depicted in FIG. 1B.

The micro-scale protuberances 104 should be high enough so that a water drop does not touch the micro-scale depressions between adjacent protuberances 104. In the embodiment of FIG. 1A, the micro-scale protuberances 104 may comprise a height H of between about 1 to about 100 microns and a diameter D of between about 1 to about 50 microns, wherein the fraction of the surface area of the substrate 108 covered by the protuberances 104 may range from between about 0.1 to about 0.9. The nano-scale protuberances 112 may comprise a height h of between 1 nanometer to about 1 micron and a diameter d of between 1 nanometer to about 0.5 microns, wherein the fraction of the surface area of the substrate 108 covered by the protuberances 112 may range from between about 0.1 to about 0.9. The nano-scale structure 110 may be disposed primarily on the micro-scale protuberances 104, or alternatively primarily on the micro-scale depressions 106, or primarily uniformly across micro-scale structure 110.

The pitch P between adjacent micro-scale protuberances 104 or depressions 106 may range from between about 1 and about 500 microns. The pitch p between adjacent nano-scale protuberances 112 or depressions 114 may range from between 1 nanometer and about 10 microns.

The arrangement of hierarchical structures may be geometric or describable generally with a mathematical equation, as provided above. Alternatively, the hierarchical structures may be randomly disposed, possibly with varying pitch, which is more typical of natural structures. The arrangement of hierarchical structure can generally be described by a fractal dimension, F. A fractal dimension is a statistical quantity that gives an indication of how completely a collection of structures appears to fill space, in the present case a plane, as one examines that structure on a multiplicity of spatial scales.

Specifying a fractal dimension, which is statistical in nature, does not necessarily indicate that the hierarchical structure is well defined by a mathematical equation. Generally, a random arrangement of structures within a specific scale possesses a higher fractal dimension than one in which the structure is mathematically described at all points on a surface. Thus, a random structure may possess an advantage in the aspect that a synthetic structure of the present disclosure has greater utility when interacting with a natural surface such as tissue. A higher fractal dimension within a specific spatial scale may be achieved by applying to a substrate multiple pitch arrangements. The protuberances and depressions may be locally scaled with respect to the local pitch. Accordingly, the pitch may vary within a scale structure. In the practical realization of higher fractal dimension structures, the variation of the pitch may be describable by a mathematical equation, for example, a sinusoidal variation of pitch, which would have utility in mimicking natural surfaces.

Generally, structures can be described as sharp-edged or rounded, and this feature is not typically captured by a fractal dimension. On the other hand, a Fourier decomposition of such structures would provide a fractal-like dimension. For example, a sharp-edged structure would require a greater number of sinusoidal waveforms to describe such a structure in superposition. This corner roundness can be characterized by a radius (R,r), and generally may be different in a direction x relative to an orthogonal direction y in the plane of the implant.

Another structural aspect not addressed by the above descriptive parameters is the degree of communication between structures. By communication, it is meant that a structure, such as a protuberance or a depression, has a spatial extent greater than the pitch. For example, a valley surrounding a protuberance may be connected to another valley surrounding another protuberance, thus the depressions are said to be communicating whereas the protuberances are not. The degree of communication or connectedness c or C (nano-scale or micro-scale, respectively) can be quantified by the ratio of the spatial extent in one direction, for example Dx, and the pitch in an orthogonal direction, for example Py. Accordingly, $Cx=Dx/Py$ and $cx=dx/py$. Furthermore, the communication can vary across the surface of the substrate. The communication may range from 1 to about 1000, more particularly the communication may extend over the entire surface of the substrate.

Figure 2A:
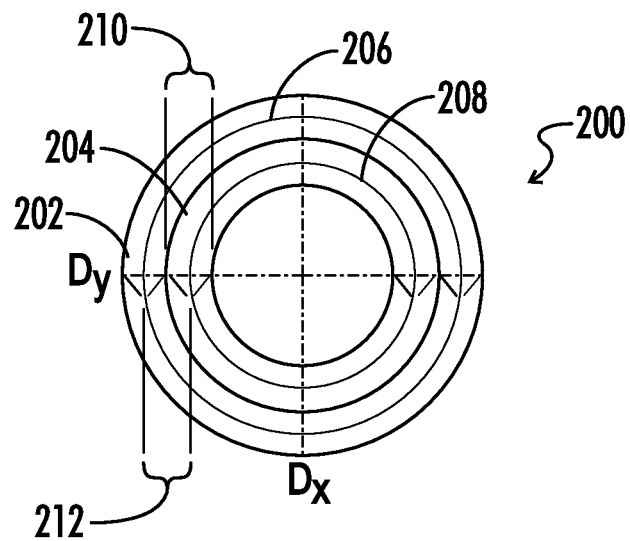
FIG. 2A. Schematic of maximum communication structure C=1.
Figure 2B:
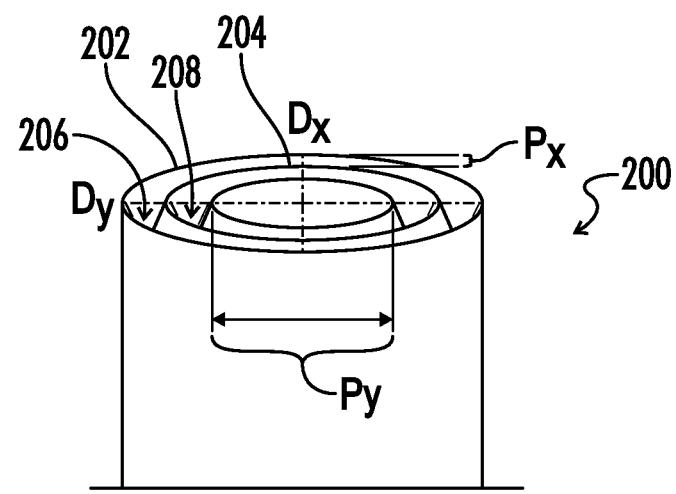
FIG. 2B. Schematic of communication structure C=0.25.
Figure 2C:
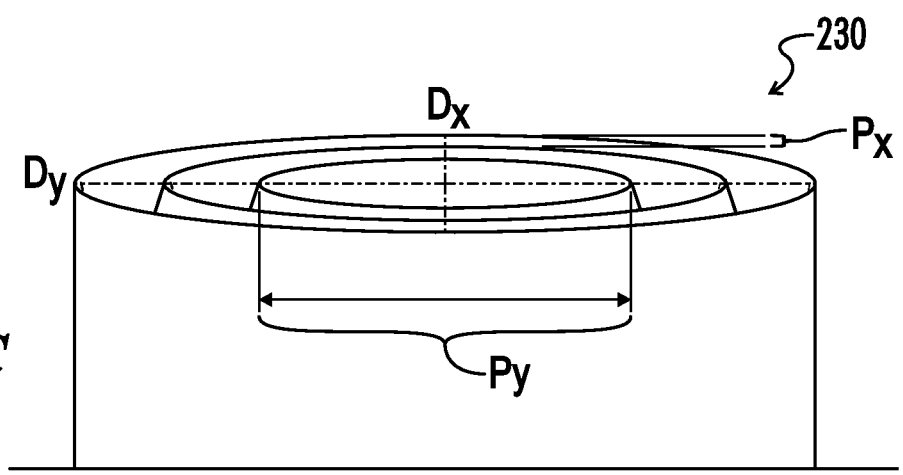
FIG. 2C. Schematic of minimum communication structure C→0.

Referring to FIGS. 2a-c, in FIG. 2a a concentric circular structure 200 is comprised of a first protuberance 202, a second protuberance 204 a first valley 206 and a second valley 208 and is characterized by Dx, Dy, Px, Py. Note for non-varying pitch, the pitch is the same whether measured peak to peak 210 or trough to trough 212. Due to the circular structure, $Dx=Dy$, $Px=Py$ and $D=P$, which gives $Cx=Cy=1$. Now referring to FIG. 2b, wherein the structure is elliptical 230. In this instance $Dx<Dy$ and $Px<Py$. Let $4Dx=Dy$, $4Px=Py$, and $Dx=Px$, then $Cx=0.25$ Now referring to FIG.

2c, wherein the structure is more elliptical 240. In this instance Dx<Dy and Px<Py. Let 100Dx=Dy, 100Px=Py, and Dy=Py, then Cx=1/100=0.01

In the limit where the valleys become parallel the communication Cx→0. Accordingly, structures of low communication can be constructed for both depressions and protuberances where reference to a flat, non-textured level is made. For example, a texture may be impressed into a flat planar surface wherein some of these textures are protuberances and other textures are depressions, separated by regions of flat planar surface. Structures can be created wherein the depressions possess a high communication ratio and the protuberances possess a low communication ratio, and conversely.

These structures are constructed with the purpose of creating Wenzel and Cassie states, on a multiplicity of scales, when the prosthetic of the present disclosure is initially implanted and at a long period after implantation.

It is known in the art that the transition to the Wenzel state can be discouraged by the use of sharp cornered features in the plane of the surface. However, the occurrence of sharp cornered structures in natural structures, such as rose petals, is less common. Natural structures tend to possess rounded surface features, especially radiused or filleted corners. In nature, resistance to conversion to a Wenzel state seems to involve the creation of involute rounded structures rather than sharp edges. By involute it is meant concavity oriented in a line not orthogonal to the substrate surface. Such structures are difficult to create by an etching or casting method, but can readily be created by an embossing method that entails folding of a structure. Similarly, the Wenzel state can be discouraged by the use of curving communications between structures as opposed to straight line communication. In most cases, higher hydrophobicity equates with lower propensity for a Wenzel transition.

Alternatively, a prosthetic may be comprised of a substrate onto which is deposited a first functional component with a discrete geometric structure and a second functional component with a second discrete geometric structure.

One of the functional components may be hydrophobic, and may contain a fluorine-containing moiety which associates with gas phase oxygen to alternatively associates with lipo-substances. The second functional component may be hydrophilic, and when implanted readily associates with water. Upon implantation, the two functional components set up domains of hydrophobic constituents derived from the implant environment and domains of hydrophilic constituents derived from the implant environment. The structure is selected such that the implant derived hydrophobic constituents bead or possess high surface tension juxtaposing the regions of implant derived hydrophilic constituents. The degree to which the implant derived constituents fill the geometry of the surface determines whether a Cassie or wettable Cassie state exists locally.

Wettable here means both the spread of aqueous components across the implant surface and the spread of lipophilic components across the implant surface. Thus, depending on the time and conditions surrounding the implant, either the aqueous or lipo fractions may be relatively more spreading. Therefore, the implant surface may be simultaneously adhesive to hydrophobic substances and repulsive to hydrophilic substances, or vice versa, and this condition may be designed to change with time. For example, the relative strengths of adhesivity and repulsivity may change with time, or the condition of adhesivity/repulsivity may switch with respect to hydrophilic or hydrophobic constituents.

Super hydrophobic surfaces relying solely on surface structure will eventually saturate with water as the gas phase entrapped on the surface dissolves into the body and by the accumulation of amphilic substanced in biologic fluids. This saturation can be delayed or prevented by the use of moieties that retain gas phase molecules, for example fluorine with an affinity for gaseous oxygen. Alternatively, lipophilic regions can be dispersed across the surface in parallel with surface morphology to encourage accumulation of lipo-substances to the exclusion of wetting by water. Thus, such stable surfaces would continue to resist shear forces.

The hydrophobicity of a surface is enhanced by the placement of exterior corners around depressions. In some embodiments, this is achieved by the creation of additional pairs of adjacent depression walls that project into and are joined at the interior of the depression. In some embodiments this is achieved by designing an ordered array of depressions of a first hierarchy (examples: triangular, rectangular, pentagonal, or hexagonal shapes, regular or irregular; and further polygonal shapes defined generally by straight line segments). A second feature of smaller size and different hierarchical order is then superimposed on the depression wall of the first pattern. The method employed in creating such a structure may involve embossing a nano-structure and then embossing a microstructure.

Alternatively, the substrate may be hydrophobic. Hydrophobic substances suitable for implantation include polyesters made from aliphatic or aromatic dicarboxylic acids and aliphatic and/or aromatic diols, e.g.: polyesters synthesized from aliphatic dialcohols having 2 to 18 carbon atoms, e.g., propanediol, butanediol, hexanediol, and dicarboxylic acids having 3 to 18 carbon atoms, such as adipic acid and decanedicarboxylic acid; polyesters synthesized from bisphenol A and the above mentioned dicarboxylic acids having 3 to 18 carbon atoms; and polyesters synthesized from terephthalic acid, aliphatic dialcohols having 2 to 18 carbon atoms, and dicarboxylic acids having from 3 to 18 carbon atoms.

The polyesters may optionally be terminated by long-chain monoalcohols having 4 to 24 carbon atoms, such as 2-ethyl hexanol or octadecanol. Furthermore, the polyesters may be terminated by long-chain monocarboxylic acids having 4 to 24 carbon atoms, such as stearic acid. In most cases, hydrophobicity is reduced by the presence of polar pendant groups, such as hydroxyls.

Alternatively, polymers containing urethane (carbamate) or urea links or combinations of these can be made hydrophobic by varying the number of these links relative to the molecular weight of the amorphous phase backbone, as well as varying the hydrophobicity of the backbone. Typically, such polymers are formed by combining diisocyanates with alcohols and/or amines. For example, combining toluene diisocyanate with a diol and a diamine under polymerizing conditions provides a polyurethane/polyurea composition having both urethane linkages and urea linkages. Such materials are typically prepared from the reaction of a diisocyanate and a polymer having a reactive portion (diol, diamine or hydroxyl and amine), and optionally, a chain extender.

Suitable diisocyanates include both aromatic and aliphatic diisocyanates such as toluene diisocyanate, 4,4'-diphenylmethane diisocyanate, 3,3'-dimethyl-4,4'-biphenyl diisocyanate, naphthalene diisocyanate and paraphenylene diisocyanate. Suitable aliphatic diisocyanates include, for example, 1,6-hexamethylene diisocyanate (HDI), trimethylhexamethylene diisocyanate (TMDI), trans-1,4-cyclohexane diisocyanate (CHDI), 1,4-cyclohexane bis(methylene isocyanate)

(BDI), 1,3-cyclohexane bis(methylene isocyanate), isophorone diisocyanate (IPDI) and 4,4'-methylenebis(cyclohexyl isocyanate).

The alcoholic or amine containing polymer can be a diol, a diamine or a combination thereof. The diol can be a poly(alkylene)diol, a polyester-based diol, or a polycarbonate diol. As used herein, the term "poly(alkylene)diol" refers to polymers of alkylene glycols such as poly(ethylene)diol, poly(propylene)diol and polytetramethylene ether diol. The term "polyester-based diol" refers to a polymer such as ethylene, 1,3-propylene, 1,2-propylene, 1,4-butylene, 2,2-dimethyl-1,3-propylene, and the like. One of skill in the art will also understand that the diester portion of the polymer can also vary. For example, the present disclosure also contemplates the use of succinic acid esters, glutaric acid esters and the like.

Useful polymers for use in construction of the present disclosure include, for example, hydrophobic monomers olefins, cyclooletins, fluoroolefins, fluorochloroolefins, vinyl aromatics, diolefins such as butadiene, isoprene and chlorobutadiene, and different monoethylenically unsaturated monomers that contain at least one alkyl group.

Suitable polyalkylene backbones for polymer construction include olefins such as ethylene, propylene, n-butene, isobutene, n-hexene, n-octene, isooctene, n-decene and isotridecene.

Hydrophobic monomers may be further synthesized by the addition of fluorine, for example, fluorinate polyalkylene polymers such as fluoroolefin, fluorochloroolefins such as vinylidene fluoride, chlorotrifluoroethylene and tetrafluoroethylene.

These polymeric constituents may be linked together in self-organizing networks or in chain-extended networks, crosslinked or not, using urea or urethane links. Such links are typically formed using low molecular weight diisocyanates, but higher functional isocyanates are also useful in achieving the polymeric networks of the present disclosure.

Bioabsorbable links may also be incorporated into the polymer network. Functional ends on the hierarchical structures of the present disclosure may be capped with bioactive moieties, for example, boswellic acid or hyaluronate.

The polymers of the present disclosure may be combined with biofunctional substances. In particular, implants with a texture-induced migration resistance may be clinically augmented by addition of a bacteriocidal group. Examples of bacteriocides include silver sulfadiazine, chlorhexidine, glutaraldehyde, peracetic acid, sodium hypochlorite, phenols, phenolic compounds, iodophor compounds, quaternary ammonium compounds, and chlorine compounds, in addition to clinically useful antibiotics.

In construction of a hierarchical morphology and also depositing a hydrophobic/hydrophilic structure, a cast of a suitable hierarchical structure may be used. For example, a crystalline structure or a cast of a biologic surface known to have such structure. Suitable biological surfaces include petals, for example red rose petals, and leaves, for example lotus leaves. The cast can be made with a hydrophobic substance that can be latter removed from a surface formed thereon. A suitable casting medium might be methylcellulose.

Figure 3A:
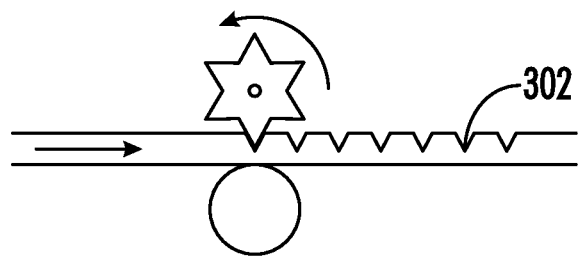
FIG. 3A-B. A method of manufacture of an implantable prosthetic of the present disclosure.
Figure 3B:
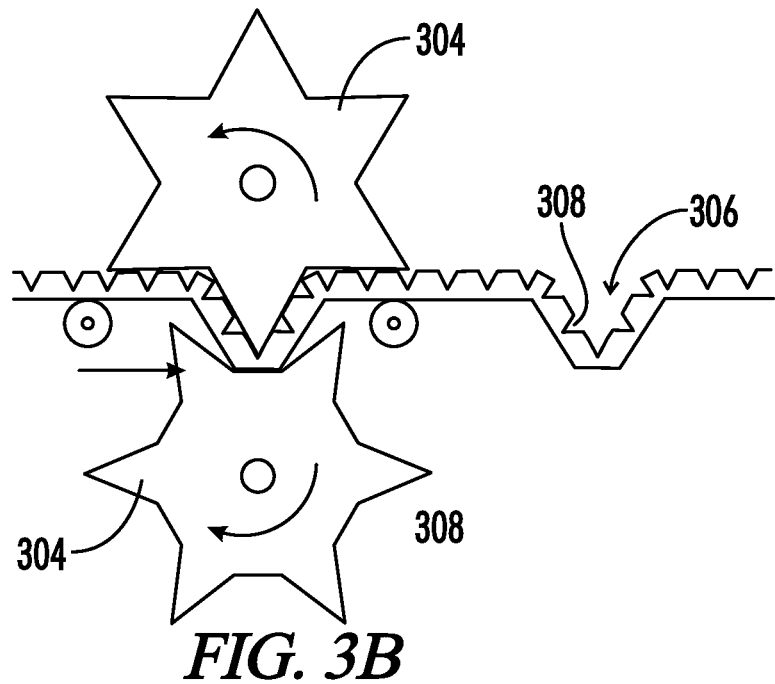

The methods of manufacture of an implantable prosthetic of the present disclosure include lithography, casting, extrusion/embossing, and any of several methods for transferring a texture to a surface. A preferred method is embossing. Referring now to FIG. 3, a polymeric substance is heated to a molten state and passed through dual rollers, at least one of which contains a negative image of the desired embossed structure. In the instance of FIG. 3, a nano-scale texture 302 is embossed on a formed planar sheet 300, as depicted in FIG. 3a. As depicted in FIG. 3b, formed sheet 300 is heated to a malleable but not fluid state and passed through dual rollers 304 possessing a micro-scale texture 306 which impresses an inverse image. The micro-scale texture 306 is large relative to the nano-scale texture 302, thus the impression of the micro-scale texture 306 folds the nano-scale texture 302, making possible involute structures 308. The method depicted in FIG. 3 may be improved by heating from the non-textured side, so that the textured side is cooler and the nano-scale texture is less likely to be deformed by impressing the micro-scale texture over the nano-scale texture.

Surface textures from fluorinated polyalkyelene polymers of specific molecular weight may be constructed by chain extension of tetrafluoroethylene using diisocyanates in ratio that provides separate polymers chains of a desired length. This solution can then be suspended in water and precipitated on a casting surface of methylcellulose. Once the cast surface is coated with hydrophobic polymeric chains, the water can be removed and the surface dried, and a self-assembling prepolymer of triol of ethylene oxide/propylene oxide endcapped with isocyante can be polymerized on the surface, which then incorporates the fluoro-polymer in the polymerized volume. Subsequently the methylcellulose mold is dissolved with ether to provide a surface of hierarchical structure.

Other methods of making a structured surface to be used as a template involve multi-phase deposition, chemical or photo etching, the use of metal powders, fibers and the like deposited on a surface in a specific areal density. Furthermore, the polymeric structure itself may be comprised of alternating hydrophobic and hydrophilic units, the density and distribution of these units being selected by appropriate choice of molecular weight of the monomeric units and fraction ratios. Thus, a surface texture may comprise both spatially varying materials with different hydrophobicity and topological textures.

In particular, a multiplicity of structural and/or hydrophilic-hydrophobic states may be selected not only to span at least one order of magnitude in size or distribution, but these scales may be related in a self-similar way and may possess a fractal dimension. Particular fractal dimensions may be useful in their repulsive effect, and others may be useful in their attractive effect.

Other approaches may include absorbable polymers designed to transition from a Cassie state to a wettable Cassie state and finally to a Wenzel state. For example, grooves in an absorbable substrate of at least two scales are made which are non-communicating. As the substrate absorbs, the individual grooves begin to form communicating interfaces which transition into a wettable Cassie state. As the microstructure breaks down further, the surface becomes increasingly proximal to surrounding water, and eventually enters a Wenzel state. For example, a Cassie to Wenzel state can be achieved when the ratio of groove height to groove width decreases.

Additionally, a desired surface may be coated with a water-soluble lipophilic substance which provides the desired phase separate components between aqueous biologic fluid and the solubilized coating, such that the solubilized coating beads on the implant surface subsequent to implantation. Alternatively, the coating may be partially bioabsorbable, which fractionates into the nano or micro particles that then associate with the implant surface according to its surface structure to form the desired Cassie state in vivo.

A desired Cassie state of the present disclosure may be achieved by forming a foam with a multiplicity of porous dimensions. The desired distribution of porous dimensions may be realized as a consequence of temperature, pressure or changes in viscosity as the prepolymers polymerizes. Alternatively, the prepolymers may be crosslinked in the presence of nucleating particles of different size. In particular, an isocyanate prepolymer may be used which liberates gas phase carbon dioxide when mixed with water. The reaction may precipitate out of water suspension as it polymerizes forming a layer, or may polymerize entirely in its volume, after which the water is removed. Accordingly, the desired Cassie state of the present disclosure may be achieved not only on a surface but also throughout a volume. These three-dimensional Cassie volumes are of particular use in tissue scaffold applications. Such scaffolds may be bioabsorbable or permanent.

The composition of the present disclosure may be free of substantially free of any optional or selected ingredients described herein.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

As used herein, the term "about" should be construed to refer to both of the numbers specified in any range. Any reference to a range should be considered as providing support for any subset within that range.

Examples are provided to illustrate some embodiments of the embodiments of the present disclosure but should not be interpreted as any limitation thereon. Other embodiments within the scope of the claims herein will be apparent to one skilled in the art from the consideration of the specification or practice of the embodiments herein. It is intended that the specification, together with the example, be considered to be exemplary only, with the scope and spirit of the disclosure being indicated by the claims which follow the example.

EXAMPLES

In these examples the following variables will be used to describe the surface texture. An upper case variable denotes that variable measured on a large scale, and a lower case variable denotes that variable measured on a smaller scale. By extrapolation, structures comprising more than two texture scales are anticipated. Height (H) is measured on the structure of largest connectedness (C) value, whether it be a positive (protuberance) or negative (valley) structure. The variables x and y denote orthogonal coordinates in the plane of the surface of the device. A variable associated with another variable in parentheses denotes the first variable is a function of a second variable, for example $F(x)$ denotes the fractal dimension varies as a function of the spatial dimension x.

H,h=height, measured orthogonal to the plane of the surface, peak to trough
D,d=diameter, measured in the plane of the surface, 2×lateral peak to trough, x and y values
P,p=pitch, measured in the plane of the surface, peak to peak, x and y value
F,f=fractal dimension
R,r=corner radius, x and y values
C,c=connectedness Example 1

A planar implant comprising a tissue adhesive surface on one side and a tissue anti-adhesive surface on the other side. The implant may possess holes that pass through the planar implant allowing for tissue to grow through the implant. In this aspect, the present example is novel in functionality in that the tissue through-growth does not promote tissue adhesion to adjacent tissue surfaces since it is well vascularized tissue which is distinct from scar tissue which is not well-vascularized and tissue adhesive.

Accordingly, the above implant may possess a petal effect on the tissue adhesive side and a lotus effect on the tissue anti-adhesive side. The anti-adhesive side would be super hydrophobic, possessing a surface texture with spatially hierarchical roughness, wherein the contact angle at every scale of surface roughness is substantially of Cassie type. The tissue adhesive side would be super hydrophobic, possessing a surface texture with spatially hierarchical roughness, wherein the contact angle at some scales of surface roughness is substantially of Cassie type and at other scales of roughness is of Wenzel type. In particular, those scales of surface roughness that on average are spatially larger are predominately of Wenzel type. Those scales of surface roughness that are on average spatially smaller are predominately of Cassie type.

Variations on the present example characteristically possess a large contact hysteresis on the tissue adhesive side and a relatively smaller contact hysteresis on the tissue anti-adhesive side. Further variations of the present example characteristically retain their respective contact hysteresis on each side of the implant due to a contact equilibrium that is established by the combination of hydrophobicity hierarchically scaled structures and surface roughness hierarchically scaled structures.

Example 2

A surgical barrier comprised of a nonporous layer which on one side possesses a high contact hysteresis angle and on the other side possesses a low contact hysteresis angle wherein first high contact hysteresis angle is sufficiently large to generate a rapid and reversible adhesion to tissue. The rapidity of adhesivity being largely determined by the energy required to form a solid/liquid interface and the ease of reversibility being largely determined by the energy required to dis-associate a solid/liquid interface.

Example 3

A tissue scaffold for soft tissue repair, wherein all surfaces are adhesive. The implant may be substantially porous to allow tissue incorporation and to direct neovascularization of the implant. The implant may be bioabsorbable. Said surfaces characteristically possess a high contact angle hysteresis. The contact angle hysteresis may be small on exterior surfaces as compared to internal porous surfaces to promote tissue incorporation without promoting excessive adjacent tissue adhesions. Alternatively, the external surface may possess a contact angle hysteresis that is greater than the internal contact angle hysteresis. Such an implant might be used in a context where greater adhesivity between adjacent tissue layers is desirable in a soft tissue repair.

Example 4

An absorbable soft tissue repair implant wherein the immediate surface has a desired texture, and as this layer is solubilized by the body, successive layers are revealed with varying surface textures. For example, an implant of the present example wherein the contact angle hysteresis reduces as the implant absorbs. Alternatively, an implant of the present disclosure wherein the contact angle hysteresis increases as the implant absorbs. The former being useful in a surgical application where native tissue healing is aggressive, either by virtue of a robust physiology or due to the position of the implant within the body. The later, being useful in a surgical application where native tissue healing is weak, either by virtue of a genetic or pathological condition wherein certain types of collagen are inadequately synthesized or due to the position of the implant within the body.

Alternatively, variations of the present example may possess variable contact angle hysteresis either spatial or at depth within the absorbable implant. For example, both the value of the contact angle hysteresis may vary as well as the thickness or mass of adjacent layers of singular contact angle hysteresis.

Example 5

Implants of Example 1-4 wherein at least part of the implant is comprised of fluoro-hydrocarbons. For example, polyurethane synthesized with a fluoro diisocyanate. Alternatively, polyurethane synthesized with a polyol wherein at least some of the carbons are replaced by fluorine.

Example 6

Implants of Examples 5 wherein oxygen is adsorbed to the implant prior to implantation, thereby locking to the implant surface a gaseous phase comprised substantially of oxygen. This oxygen could be released over a period of time in vivo, thus further promoting tissue infiltration of the implant. Additionally, the surface oxygen may impede or kill various types of bacterial colonization. Lastly, said attached oxygen could benefit a soft tissue repair which is characteristically avascular or temporarily devoid of systemically supplied oxygen.

Example 7: Implant where the Surface Texture Satisfies D not Equal to P

A regular array of protuberances or valleys with height H, wherein the diameter D of the protuberances or valleys is different from the spacing P between such structures.

Example 8: Implant where the Surface Texture Possesses Sinusoidally Varying Height A regular array of approximately conical protuberances or valleys with height $H(x,y)=A \sin(x,y)$, where $\sin(x,y)$ can denote any of $\sin(x)+\sin(y)$, $\sin(x)\sin(y)$, $\sin(xy)$, $\sin(x+y)$.

Example 9: Implant where the Surface Texture Satisfies D(x) and P=Constant

A regular array of approximately conical protuberances or valleys with varying diameter $D(x,y)=A \sin(xy)$ and constant distance between protuberances or valleys P.

Example 10 Implant where the Surface Texture Satisfies P(x) and D=Constant

A regular array of approximately conical protuberances or valleys with varying spacing $P(x,y)=A \sin(xy)$ and constant protuberance or valley diameter D.

Example 11: Implant where the Surface Texture is a Koch Snowflake

The surface constructed by starting with an approximately conical protuberance or valley, then recursively altering each protuberance or valley as follows:
1. Draw two line segments, running peak to trough, intersecting the peak orthogonally (see FIG. 7A);
2. divide each line segment into three segments of equal length;
3. Place a conical protuberance or valley centered on each of the middle segments of step 2 (see FIG. 7B);
4. Repeat steps 1-3 on the protuberances or valleys of step 3. (See FIG. 7C). The resulting shape is shown in cross section in FIG. 7D with fractal dimension F=1.26.

Example 12: Implant where the Surface Texture is a Sierpinski Gasket

An algorithm for obtaining arbitrarily close approximations to the Sierpinski triangle is as follows
1. Tile the implant surface with maximal sized triangles;
2. Shrink the triangle to ½ height and ½ width, make three copies, and position the three shrunken triangles so that each triangle touches the two other triangles at a corner;
3. Note the emergence of the central hole (FIG. 4);
4. Apply step 2 to the largest remaining triangles.

Figure 4:
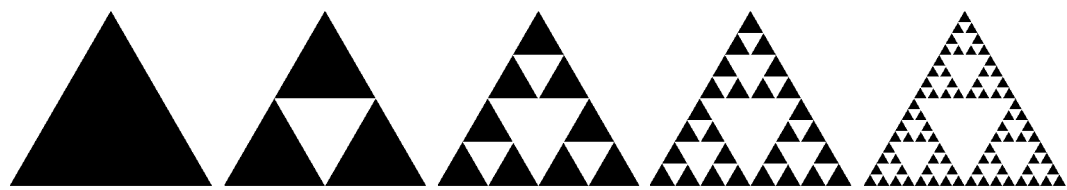
FIG. 4. Example of Sierpinski gasket surface texture.

Replace the triangles with either tetrahedrons or cones, either positive or negative (FIG. 4). The resulting structure has fractal dimension F=1.59.

Example 13: Implant where the Surface Texture is an Apollonian Gasket

Figure 5:
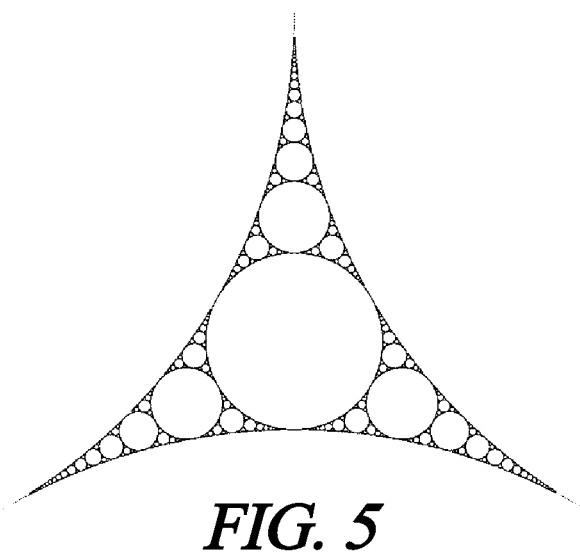
FIG. 5. Example of Apollonian gasket surface texture.

Tile the implant surface with three circles $C_1$, $C_2$ and $C_3$, each one of which is tangent to the other two (these three circles can be any size, as long as they have common tangents). Apollonius discovered that there are two other non-intersecting circles, $C_4$ and $C_5$, which have the property that they are tangent to all three of the original circles—these are called Apollonian circles. Adding the two Apollonian circles to the original three, we now have five circles (FIG. 5).

Take one of the two Apollonian circles—say $C_4$. It is tangent to $C_1$ and $C_2$, so the triplet of circles $C_4$, $C_1$ and $C_2$ has its own two Apollonian circles. We already know one of these—it is $C_3$—but the other is a new circle $C_6$.

In a similar way we can construct another new circle $C_7$ that is tangent to $C_4$, $C_2$ and $C_3$, and another circle $C_8$ from $C_1$, $C_3$ and $C_1$. This gives us 3 new circles. We can construct another three new circles from $C_5$, giving six new circles altogether. Together with the circles $C_1$ to $C_5$, this gives a total of 11 circles.

Continuing the construction stage by stage in this way, we can add $2.3^n$ new circles at stage n, giving a total of $3^{n+1}+2$ circles after n stages. In the limit, this set of circles is an Apollonian gasket.

The Apollonian gasket has a fractal dimension F=1.3057. The circles can be replaced with positive or negative cones.

Figure 6:
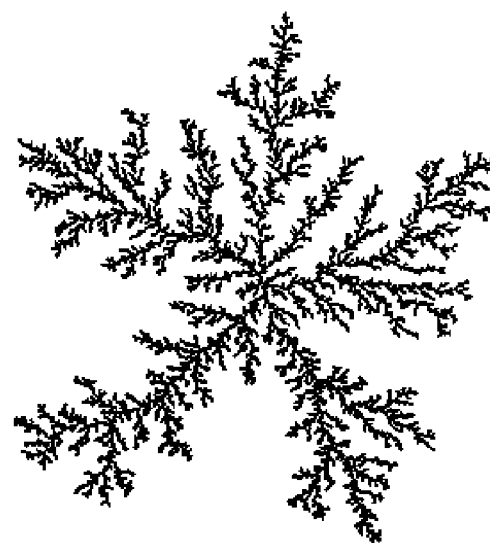
FIG. 6. Example of a petal-mimic surface texture.

Example 14: Implant where the Surface Texture is a Diffusion Limited Aggregation The implant surface was partitioned into an approximately circular grid of square cells. The cell at the center of the circle is the location of the seed point. Now pick a square on the perimeter of the grid and place a random function on that square. Randomly, advance the state of the function to one of the four adjacent squares. If this function leaves the implant surface another seed point is started, chosen randomly at the edge. When the function arrives at one of four squares adjacent to the seed point, it stops there forming a cluster of two seed points, each releasing a new function. Continuing in this way builds an aggregate illustrated in FIG. 6. Now replace the linear trace with either a protuberance or a valley, generally these structures are inscribed on a larger scale structure of conical protuberances or valleys.

Figure 9:
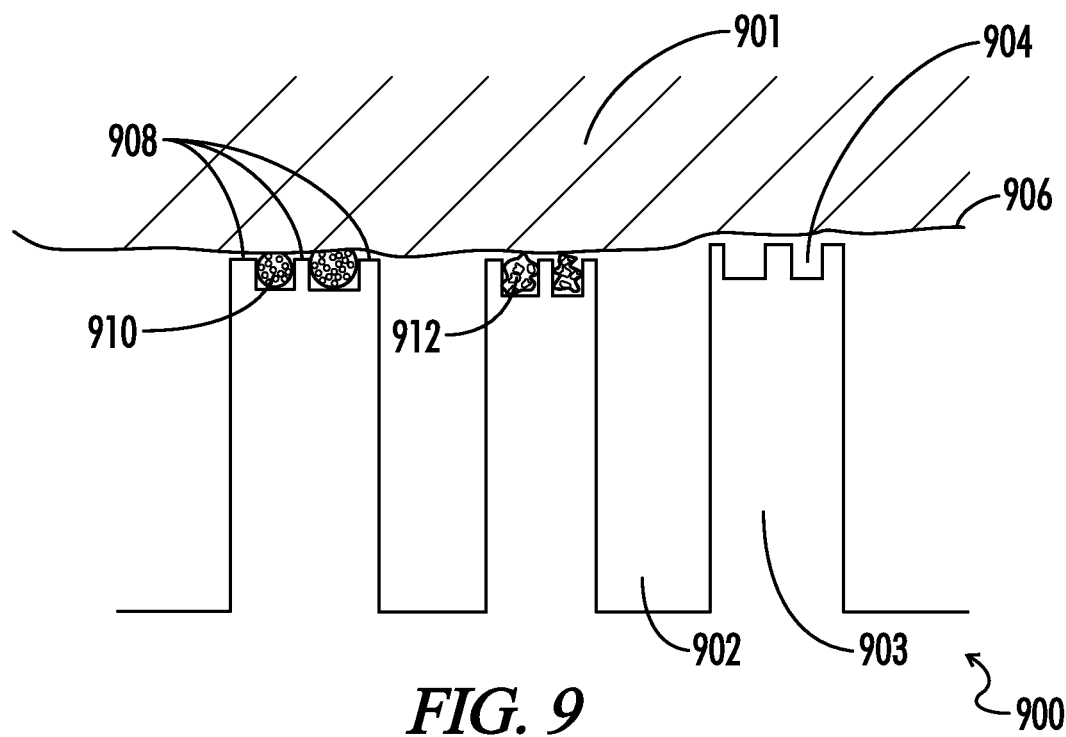
FIG. 9. Example of an implantable where the surface texture makes the implant hydrophobic to reduce the rate of absorption.

Example 15: Implant where the Surface Texture Makes the Implant Hydrophobic to Reduce the Rate of Absorption The disclosure relates to implantable, absorbable sheets which are hydrophilic, and possibly swell or even dissolve in situ, whereby the addition of a hydrophobic structure reduces the rate of absorption or conformal change in situ. Accordingly, two scales of depressions, approximately cylindrical or conical are preferred. Referring to FIG. 9, a textured surface 900 interface with tissue 901 comprises first scale depressions 902 and first scale protuberances 903 and second scale depressions 904. Water layer 906 interacts only with ridges 908 formed by the first scale 902 and second scale 904 structures. Air 910 and later lipids 912 surround the second scale features. Thus, the surface area presented to water is significantly reduced.

Example 16: Absorbable Hydrophobic Implantables Made Hydrophilic

Figure 10:
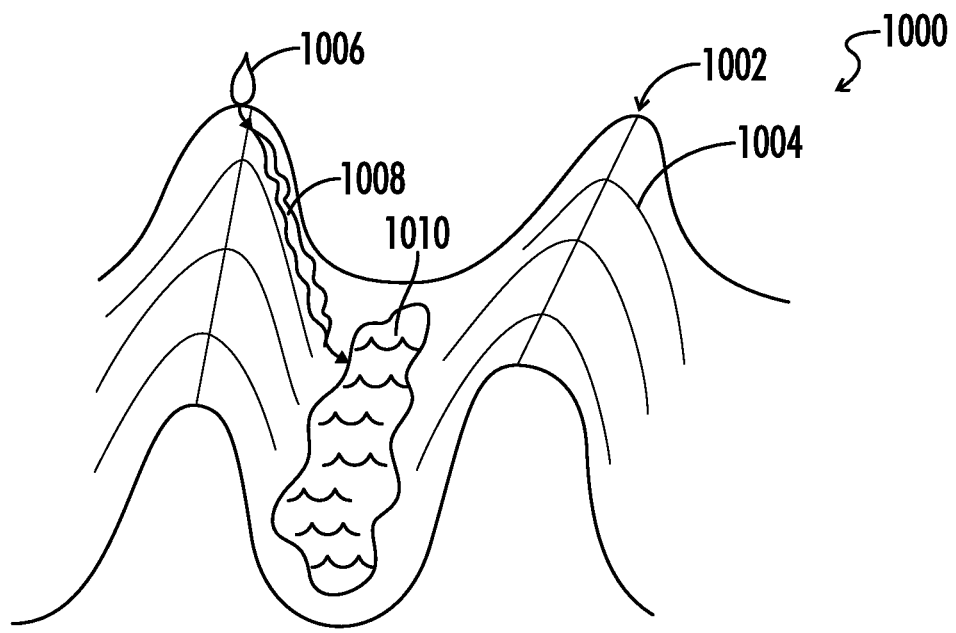
FIG. 10. Example of an implantable where the surface texture makes the implant hydrophilic.

Alternatively, the disclosure relates to physiologically absorbable, generally fibrogenic, hydrophobic materials that are made relatively hydrophilic during a first interval by the addition of surface texture. Structures of this type resemble corals. Accordingly, two scales of ridges, with a high connectedness number and tortuosity are preferred. Referring to FIG. 10, a textured surface 1000 comprises first scale ridges 1002 and orthogonally arranged second scale ridges 1004. Water layer 1006 wicks 1008 first into small scale ridges 1004 which drains 1010 into large scale ridges 1002. Eventually the entire implant surface is coated with a thin layer of water, which without the surface texture would have been coated by protein.

Figure 11:
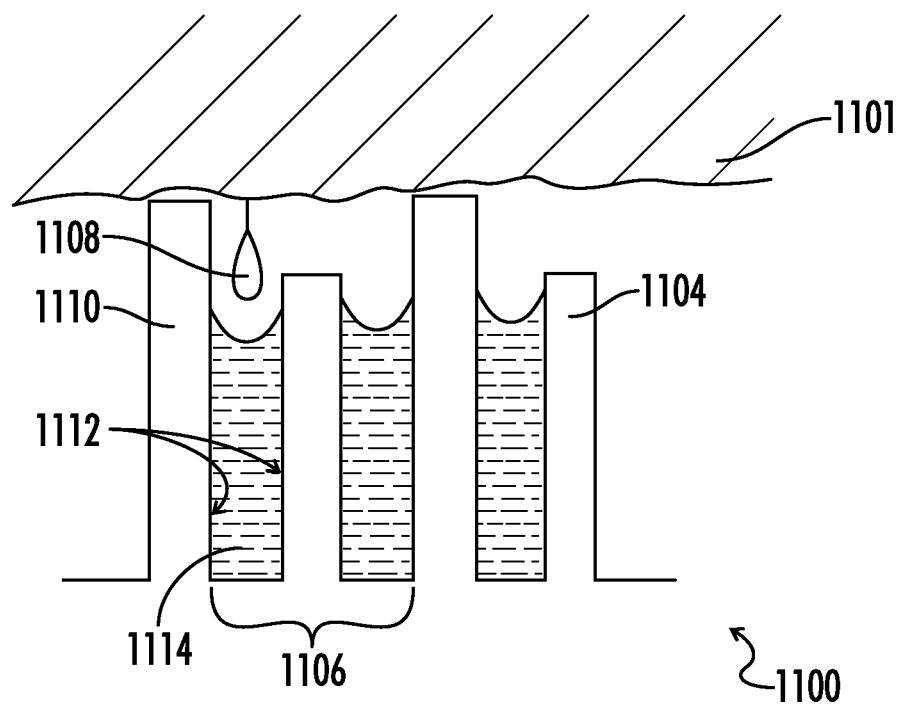
FIG. 11. Example of an implantable where the surface texture makes the implant hydrophilic to increase the rate of absorption.

Example 17: Absorbable Hydrophobic Implantables Made Hydrophilic to Increase the Rate of Absorption Alternatively, the disclosure relates to hydrophobic implantable sheets that do not absorb quickly in the body, which are made to absorb more quickly with the addition of a hydrophilic structure. Accordingly, two height scales of pillars are preferred. Referring to FIG. 11, a textured surface 1100 interacting with tissue 1001 comprises first scale pillars 1102 and between these second scale pillars 1104. The first scale pillars form spaces 1106 which induce a capillary effect 1108, and actively draw water 1108 into the spaces 1106 as the implant material dissolves into the water 1110. The second scale pillars 1104 form smaller spaces 1112 that further drive water 1114 deeper into the substrate. Hence, the surface area in contact with water is significantly increased.

Example 18: Implantables with at Least One Side Immediately Tissue Adhesive

Surgical barrier implants block tissue adhesions between adjacent layers of tissue. Due to their anti-adhesive functionality, they tend to migrate after implantation requiring localization by suture or staple. These localization points then become foci for tissue adhesion. A combination of Wenzel and Cassie states creates a Cassie wetting condition characterized by a large contact angle hysteresis. Accordingly, these textures are not energetically favored to slide across a surface.

Figure 8:
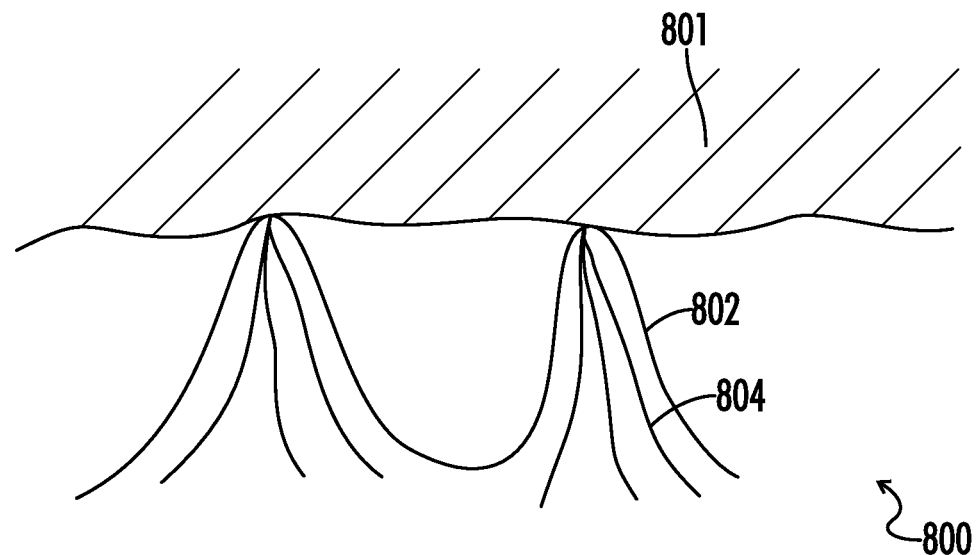
FIG. 8. Example of an implantable with at least one side immediately tissue adhesive.

Referring to FIG. 8, a Cassie wetting texture 800 interacting with tissue 801 is comprised of first scale protuberances 802 and second scale ridges 804 oriented axially with protuberances 802 and distributed circumferentially. The ridges 804 enter the Wenzel state when placed on tissue. The Wenzel state is prevented from moving in the plane of the implant by the adjacent Cassie states created by the protuberances 802.

Efficacy Studies

Example 19

The following are efficacy studies carried out on petal structures of the present disclosure, in particular regarding shear forces.

In a first study, we made casts directly from organic red T-rose petals. Direct casts reproduce the surface texture as a negative of the original pattern. Positive casts were made by creating a negative mold and then casting a positive from the negative mold.

A number of casting materials were tested, including hot wax, wax in toluene, nail polish, hot glue, cyanoacrylate, plaster, polylactic acid (PLA 708, Boehringer-Ingelheim), silicone rubber, and pyroxylin. Only the latter three were successful, the silicone rubber being the most dependable in terms of reproducing the petal surface.

A limited shear test was performed with a small quantity of positive image PLA sheets. The procedure consisted of forming a negative pyroxylin cast, pouring PLA acetone solution over the negative cast, and dissolving away with ethanol the pyroxylin portion. Later we used silicone to create the negative mold, with similar results.

Mechanical localization (shear stress) was assessed. Cutlets of bovine "steak" were purchased and sliced into 3 cm cubes and affixed to a localized platform. The meat was kept well hydrated with physiologic saline solution at 22° C. Test articles were cut to 1×1 cm squares and mounted on discs to which was attached the filament through which force would be applied to the test article. Shear was measured by placing the strip on the 3 cm cube of meat and pulling parallel to the surface. Thus, these measurements yield a force per unit area (1 cm$^2$). In preliminary testing, there was no difference in shear force immediately vs 1 hour later. Thus, there was no observable saturation effect, and shears were not measured at different time intervals.

Two wetting scenarios were tested. In one scenario, the tissue surface was kept moist to replicate normal surgical conditions (wet to touch), but no standing water. In another, the tissue and test articles were immersed in water. The buoyancy of the disc support was minimal. However, a rather more complicate pulley system was employed for testing in water, which in the worst case should result in lower shear forces since the resistance to shear would be communicated less efficiently to the sensor, and thus the force measured lower.

In all measurements, clear outliers were discarded, and when possible, the run was repeated with additional test articles.

An Instron Mini 55 was used to record force and the crosshead speed was 0.1 cm/sec. The load cell limit was 200 g with an accuracy of +/−0.1 g.

Shear Force Measurement

All measurement rounded to nearest gram. All measurements were done with a 0.5 gram disc. All measurements were done with fresh casts to avoid texture filling, but variations in thickness could contribute to variable changes. Whenever possible, experiments comparing different attributes were done with casting made at the same time to avoid changes in casting solution or ambient conditions. Results are summarized in Tables 1-4.

TABLE 1

Negative Vs Positive

| Texture | Shear (submerged in water) (grams force) |
|---|---|
| Negative of organic rose (PLA) N = 3 | 105 +/− 36 |
| Positive of organic rose (PLA) N = 3 | 37 +/− 12 |

TABLE 2

Pyroxylin Vs PLA Casts

| Texture (negative) | Shear (submerged in water) (grams force) |
|---|---|
| Pyloxyrin of organic rose (N = 5) | 79 +/− 32 |
| PLA of organic rose (N = 5) | 107 +/− 35 |

TABLE 3

Kinetic Vs Static Shear Force - Tissue submersed in water

| Texture (negative, PLA, organic rose) | Shear (submerged in water) (grams force) |
|---|---|
| kinetic (N = 10) | 101 +/− 22 |
| Static (N = 10) | 119 +/− 35 |

TABLE 4

Wet tissue

| Texture (negative, PLA, organic rose) | Shear (wet) (grams force) |
|---|---|
| kinetic (N = 10) | 27 +/− 11 |
| Static (N = 10) | 32 +/− 9 |

Shear Tests of Manmade Patterns

All measurement rounded to nearest gram. All measurements were done with a 0.5 gram disc. All measurements were done with fresh casts to avoid texture filling. The following are tests conducted using silicone molds cast directly from organic rose and from manmade designs. The casts from the waffle design were comprised of 10- and 20-micron square depressions separated by 5-micron walls. The casts from the pillar design were comprised of 5-micron diameter and 15-micron tall cylinders spaced in two-dimensions on 20-micron centers. The casts from the Hrose design were 10-micron tall pyramids with 15-micron square bases spaced in two dimensions on 20-micron centers. The above are the positive states, and the negative states would be the spatial inverse. For example, pillars would become cylindrical depressions.

The Hrose patterns were made by a lithography process on silicon wafers. We made two silicon molds (run 1 and run 2) from which were made silicone molds. Results are summarized in Table 5.

TABLE 5

Negative Vs Positive

| Texture | Shear (submerged in water) (grams force) |
|---|---|
| 10 micron waffle (PLA) N = 3 | Not measurable |
| 20 micron waffle (PLA) N = 3 | 5 +/− 5 |
| Pillar (PLA) N = 3 | 5 +/− 5 |
| Hrose positive run 1 (PLA) N = 3 | 61 +/− 18 |
| Positive from silicone organic rose (PLA) N = 3 | 117 +/− 15 |
| Hrose positive run 2 (PLA) N = 3 | 56 +/− 21 |

The effect of using different viscosity solutions of PLA and a polyurethane (AP1959) as casting materials was studied regarding shear force. High viscosity was 1000 cps and low viscosity was 10 cps. Results are summarized in Table 6:

TABLE 6

| Texture | Moist meat (grams force) |
|---|---|
| High Viscosity positive Hrose run 2 (PLA) N = 3 | 58 +/− 14 |
| High Viscosity positive Hrose run 2 (AP1959) N = 3 | 33 +/− 9 |
| Low Viscosity positive Hrose run 2 (PLA) N = 3 | 84 +/− 29 |
| Low viscosity positive Hrose run 2 (AP1959) N = 3 | 47 +/− 14 |
| Low viscosity positive Hrose run 2 (PLA) + methylcellulose | 120 +/− 11 |
| Low viscosity positive Hrose run 2 (AP1959) + methylcellulose | 127 +/− 16 |

The Hrose patterns impregnated with methylcellulose provided the highest shear forces. The methylcellulose acts as an initiator for the formation of a hydrophobic Wenzel state.

In a last study, a nickel coated silicon mold was made with 52 different 1 cm×1 cm surface patterns. The shear forces for these patterns were measured. Initial test of the adhesivity of PLA cast patterns on pork chop were disappointing. It was concluded the patterns were too fine to provide adhesion to muscle tissue. Turning to the adhesivity on pericardium, which is very flat, it was decided to adopt a more pericardia-like surface. Egg white (albumin) was separated and slowly microwaved to provide a smooth protein surface.

Adhesivity was measured by attaching suture to an individual PLA cast textured square. The square was weighted with a 1-gram disc and placed on the albumin sheet. The suture was directed horizontally to a pulley and passed over the pulley and directed vertically. At the terminus of the suture a 25 g weight was attached. The weight was placed on a digital scale. A platform comprising the test sample and pulley was arranged on a lift that could be mechanically raised vertically. Thus, when the platform was raised, weight is transferred to the specimen, and the resulting reduction of weight on the scale was recorded at the minimum.

The adhesivity was measured 10 times, and the mean and standard deviation recorded. The pattern descriptions and adhesivity measurements are described in Table 7.

TABLE 7

Pattern Descriptions (dimensions in microns).

| Pattern | Dimensions | Adhesivity |
|---|---|---|
| Triangles | | |
| Pattern 1, 6 | 20 × 20 × 20 | 0 2.3 +/− 0.7 |
| Pattern 2, 7 | 20 × 40 × 40 | 2.1 +/− 0.5 9.8 +/− 1.2 |
| Pattern 3, 8 | 20 × 80 × 80 | 0 5.3 +/− 0.6 |
| Lines | | |
| 11, 13 | 30 wide, 30 space | 10.3 +/− 0.9 15.2 +/− 1.1 |
| 12, 43 | 30 wide, 10 space | 2.4 +/− 0.8 6.1 +/− 0.8 |
| 27, 34 | 30 wide, 60 space | 2.2 +/− 0.6 5.6 +/− 0.6 |
| 15, 50 | 5 wide, 5 space | 0 11.2 +/− 1.2 |
| 16, 51 | 5 wide, 10 space | 5.6 +/− 1.1 17.2 +/− 2.4 |
| 17, 52 | 5 wide, 20 space | 6.1 +/− 1.0 1.1 +/− 0.3 |
| 23, 41 | 10 wide, 10 space | 4.7 +/− 0.7 2.4 +/− 0.7 |
| 24, 47 | 10 wide, 20 space | 2.3 +/− 0.6 5.5 +/− 0.9 |
| 25, 48 | 10 wide, 40 space | 2.7 +/− 0.7 0 |
| Columns | | |
| 5, 32 | 10 wide ¼ circle, 10 inner radius, jagged | 5.3 +/− 0.8 8.2 +/− 1.3 |
| 19, 31 | 10 wide, ¼ circle, 10 inner radius | 5.8 +/− 0.9 8.9 +/− 1.2 |
| 29, 49 | 10 wide, ½ circle, 10 inner radius (skew array) | 7.7 +/− 1.2 6.5 +/− 0.9 |
| 30, 35 | 10 wide, ½ circle, 10 inner radius (rectangular array) | 3.1 +/− 0.9 8.9 +/− 0.7 |
| Jagged Lines | | |
| 4, 9, | 10 10 wide, 1 side jagged, 10 space | 0 12.2 +/− 1.4 1.9 +/− 0.6 |
| 33, 40 | 10 wide, jagged, 20 space | 11.2 +/− 1.0 3.1 +/− 0.7 |
| 18, 20 | 30 wide, jagged, 30 space | 2.4 +/− 0.7 8.3 +/− 1.1 |
| 26, 28 | 30 wide, jagged, 10 space | 10.8 +/− 1.3 15.7 +/− 2.1 |
| Rectangles | | |
| 36, 42 | 120 × 30 rectangles, long side jagged | 2.4 +/− 1.1 6.4 +/− 0.8 |
| 37 | 120 × 30 rectangle, short side jagged | |
| 38 | 60 × 30 rectangle, short side jagged, 10 space | |
| 39 | 30 × 30 rectangle, 1 side jagged, 10 space | |
| 44 | 120 × 30 rectangle, 10 space | |
| 45 | 60 × 30 rectangle, 10 space | |
| 46 | 30 × 30 rectangle, 10 space | |

Results

The textures can be categorized by straight line, curved segments, straight line with saw edge, rectangles with saw edge, grid of circles (positive), grid of circles (negative), grid of triangles, and/or grid of squares. Variability occurred in multiple casts from the same texture pattern. The main causes of variation were discovered to be remnant PLA in the mold, folded/deformed texture, and poor reproducibility on saw edged structures.

All adhesivity measured as grams/cm^2. The first value is the static shear force for the first listed pattern. The second value is the static shear force for the second listed pattern. The third value is the static shear force for the third listed pattern.

What is claimed is:

1. A method of making a micropattern mold, the method comprising:
   (a) providing a first substrate;
   (b) creating a positive mold of a micropattern surface in the first substrate via photolithography;
   (c) providing a second substrate;
   (d) placing the second substrate in contact with the positive mold creating a negative mold of the micropattern surface;
   (e) providing a third substrate;
   (f) placing the third substrate in contact with the negative mold;
   (g) transferring the micropattern surface of the negative mold to the third substrate to form a second positive mold;
   (h) providing a fourth substrate;
   (i) embossing the micropattern of the second positive mold onto the fourth substrate wherein the fourth substrate comprises a polymer being biodegradable and hydrophobic, and wherein the micropattern comprises a first micropattern having a first microtexture and a plurality of second microtextures, wherein the plurality of second microtextures is hierarchically disposed about the first microtexture, the first microtexture having a height ranging from 1 micron to 100 microns and a peak-to-peak pitch ranging from 100 microns to 500 microns between the first microtexture and an adjacent second microtexture, and the plurality of second microtextures having a peak-to-peak pitch of at least 10 microns, and wherein the fourth substrate comprises a superhydrophobic surface having a contact angle of 150° while further including a sessile drop contact hysteresis angle of at least 5°.

2. The method of claim 1, wherein the first substrate comprises a silicon wafer.

3. The method of claim 1, wherein the second substrate comprises room-temperature-vulcanizing-silicone and is heated prior to contacting the positive mold.

4. The method of claim 1, wherein the third substrate comprises silicone.

5. The method of claim 1, wherein the third substrate comprises silicone.

6. The method of claim 1, wherein the fourth substrate is provided as a thin film.

7. The method of claim 1, wherein the fourth substrate comprises polylactic acid.

8. The method of claim 7, wherein the polylactic acid is provided as a thin film.

9. The method of claim 8, wherein the thin film is capable of generating a Wenzel-Cassie state such that the film adheres to a target surface via a liquid interface disposed between the film and the target surface.

10. A method of making a micropattern mold, the method comprising:
    (a) providing a first substrate comprising a silicon wafer;
    (b) creating a positive mold in the first substrate via photolithography;
    (c) providing a second substrate comprising room-temperature-vulcanizing-silicone;
    (d) heating the second substrate;
    (e) placing the second substrate in contact with the positive mold; and
    (f) creating a negative mold in the second substrate, wherein the negative mold comprises a first micropattern having a first microtexture and a plurality of second microtextures, wherein the plurality of second microtextures is hierarchically disposed about the first microtexture, the first microtexture having a height ranging from 1 micron to 100 microns and a peak-to-peak pitch ranging from 100 microns to 500 microns between the first microtexture and an adjacent second microtexture, and the plurality of second microtextures having a peak-to-peak pitch of at least 10 microns, and wherein the first micropattern is a superhydrophobic surface having a contact angle of 150° while further including a sessile drop contact hysteresis angle of at least 5 degrees.

11. The method of claim 10, further comprising:
(e) providing a third substrate comprising silicone;
(g) placing the third substrate in contact with the negative mold;
(h) transferring the micropattern of the negative mold to the third substrate thereby creating a second positive mold;
(i) providing a fourth substrate; and
(j) transferring the micropattern of the second positive mold onto the fourth substrate.

12. The method of claim 11, wherein the fourth substrate is provided as a thin film, the thin film being capable of generating a Wenzel-Cassie state such that the film adheres to a target surface via a liquid interface disposed between the film and the target surface.

\* \* \* \* \*